US012686861B2

(12) United States Patent
Bailey et al.

(10) Patent No.: US 12,686,861 B2
(45) Date of Patent: Jul. 21, 2026

(54) METHOD TO CREATE PATTERNS IN TISSUE GROWTH FOR TISSUE ENGINEERING

(71) Applicants: UNIVERSITY OF WASHINGTON, Seattle, WA (US); University of Rochester, Rochester, NY (US)

(72) Inventors: Michael R Bailey, Seattle, WA (US); Adam D. Maxwell, Seattle, WA (US); Mohamed Abdalla Ghanem, Seattle, WA (US); Diane Dalecki, Rochester, NY (US)

(73) Assignee: University of Washington, Seattle, WA (US)

( * ) Notice: Subject to any disclaimer, the term of this patent is extended or adjusted under 35 U.S.C. 154(b) by 435 days.

(21) Appl. No.: 18/365,094

(22) Filed: Aug. 3, 2023

(65) Prior Publication Data

US 2024/0043825 A1      Feb. 8, 2024

Related U.S. Application Data

(60) Provisional application No. 63/395,029, filed on Aug. 4, 2022.

(51) Int. Cl.
| | |
|---|---|
| *C12N 13/00* | (2006.01) |
| *C12M 1/26* | (2006.01) |
| *C12M 1/42* | (2006.01) |

(52) U.S. Cl.
CPC ............. *C12N 13/00* (2013.01); *C12M 33/08* (2013.01); *C12M 35/04* (2013.01)

(58) Field of Classification Search
None
See application file for complete search history.

(56) References Cited

U.S. PATENT DOCUMENTS

| | | | |
|---|---|---|---|
| 4,475,921 A | 10/1984 | Barmatz | |
| 5,902,489 A | 5/1999 | Yasuda | |
| | (Continued) | | |

FOREIGN PATENT DOCUMENTS

| | | |
|---|---|---|
| CA | 2864665 | 8/2013 |
| CN | 101955595 | 1/2011 |
| | (Continued) | |

OTHER PUBLICATIONS

Final Office Action dated Oct. 15, 2024 received for related U.S. Appl. No. 17/881,206, filed Aug. 4, 2022; 29 pages total.

(Continued)

*Primary Examiner* — William H. Beisner
(74) *Attorney, Agent, or Firm* — Christensen, O'Connor Johnson Kindness PLLC

(57) ABSTRACT

Methods and systems for creating patterns in tissue growth for tissue engineering are disclosed. In one embodiment, a method for arranging biological cells along predetermined patterns using an ultrasound includes: emitting the ultrasound by an ultrasound transducer; transmitting the ultrasound through a holographic lens toward a plurality of cells; and generating a pressure field in the predetermined patterns. The predetermined pattern includes a plurality of mutually parallel transverse planes. The parallel transverse planes are configured to entrap groups of cells of the plurality of cells. The axial pressure gradients within the parallel transverse planes are smaller than a first predetermined threshold. The lateral pressure gradients within the parallel transverse planes are larger than a second predetermined threshold. In response to generating the pressure field, the groups of entrapped cells are aligned within parallel transverse planes.

21 Claims, 13 Drawing Sheets

PATTERNED PARTICLES

(56) References Cited

U.S. PATENT DOCUMENTS

| | | | |
|---|---|---|---|
| 7,837,623 | B2 | 11/2010 | Aubry et al. |
| 8,509,928 | B2 | 8/2013 | Abate et al. |
| 9,901,753 | B2 | 2/2018 | Cain et al. |
| 10,251,657 | B1 | 4/2019 | Maxwell et al. |
| 2008/0194965 | A1 | 8/2008 | Sliwa et al. |
| 2012/0029393 | A1 | 2/2012 | Lee |
| 2013/0289593 | A1 | 10/2013 | Hall et al. |
| 2013/0301383 | A1 | 11/2013 | Sapozhnikov et al. |
| 2014/0058292 | A1 | 2/2014 | Alford et al. |
| 2016/0114193 | A1 | 4/2016 | Prus |
| 2016/0185056 | A1 | 6/2016 | Beacham et al. |
| 2016/0317842 | A1 | 11/2016 | Sliwa et al. |
| 2016/0339360 | A1* | 11/2016 | Lipkens ............. B01D 17/0202 |
| 2017/0094265 | A1 | 3/2017 | Mullins et al. |
| 2017/0226473 | A1 | 8/2017 | Chen |
| 2017/0245874 | A1 | 8/2017 | Bailey et al. |
| 2017/0296216 | A1 | 10/2017 | Du et al. |
| 2017/0311804 | A1 | 11/2017 | Herring |
| 2018/0070967 | A1 | 3/2018 | Aziz |
| 2018/0110497 | A1 | 4/2018 | Beacham et al. |
| 2018/0192990 | A1 | 7/2018 | Tanter et al. |
| 2018/0341221 | A1 | 11/2018 | Melde et al. |
| 2020/0078608 | A1 | 3/2020 | Maxwell et al. |
| 2020/0384463 | A1 | 12/2020 | Davis |
| 2021/0008394 | A1 | 1/2021 | Cain et al. |
| 2021/0101178 | A1 | 4/2021 | Kim et al. |
| 2021/0187330 | A1 | 6/2021 | Bailey et al. |
| 2021/0260578 | A1* | 8/2021 | Shirwaiker ........ B01D 17/0214 |
| 2021/0362145 | A1 | 11/2021 | Kim |
| 2021/0396712 | A1 | 12/2021 | Jimenez Gonzalez et al. |
| 2022/0082690 | A1 | 3/2022 | Lee et al. |
| 2022/0096873 | A1 | 3/2022 | Peyman et al. |
| 2022/0328032 | A1 | 10/2022 | Kim et al. |
| 2026/0028573 | A1* | 1/2026 | Aider ..................... C12M 35/04 |

FOREIGN PATENT DOCUMENTS

| | | |
|---|---|---|
| CN | 106659463 A | 5/2017 |
| CN | 110314715 | 10/2019 |
| CN | 111254076 | 6/2020 |
| CN | 111326135 A | 6/2020 |
| CN | 213098574 | 5/2021 |
| CN | 112946087 A | 6/2021 |
| CN | 112951196 A | 6/2021 |
| CN | 113018514 | 6/2021 |
| CN | 113061279 | 7/2021 |
| CN | 213722633 U | 7/2021 |
| CN | 113215101 | 8/2021 |
| CN | 113604463 | 11/2021 |
| CN | 113643683 A | 11/2021 |
| CN | 113826229 | 12/2021 |
| CN | 113941030 | 1/2022 |
| CR | 20210549 | 11/2021 |
| EP | 0134346 A1 | 3/1985 |
| EP | 3985096 | 4/2022 |
| JP | 2014198197 A | 10/2014 |
| JP | 2022017543 A | 1/2022 |
| KR | 101261298 B1 | 5/2013 |
| KR | 20170005526 A | 1/2017 |
| WO | 2006055470 A1 | 5/2006 |
| WO | 2017097417 A1 | 6/2017 |
| WO | 2019236409 A1 | 12/2019 |
| WO | 2021035679 | 3/2021 |
| WO | 2022032203 | 2/2022 |
| WO | 2022052179 A1 | 3/2022 |
| WO | 2022083432 A1 | 4/2022 |

OTHER PUBLICATIONS

Sapozhnikov et al.; "Acoustic holography as a metrological tool for characterizing medical ultrasound sources and fields"; The Journal of the Acoustical Society of America; Sep. 15, 2015; pp. 1515-1532; vol. 138; No. 3; Acoustical Society of America.

Dennis Li et al., "Design of an acoustic metamaterial lens using genetic algorithms," Oct. 1, 2012, The Journal of the Acoustical Society of America, 132, 4, pp. 2823-2833 (Year: 2012).

M. Bakhtiari-Nejad, "Passive metamaterial-based acoustic holograms in ultrasound energy transfer systems," Mar. 15, 2018, Proc.SPIE 10595, Active and Passive Smart Structures and Integrated Systems XII (Year: 2018).

J. Xia et al., "Broadband Tunable Acoustic Asymmetric Focusing Lens from Dual-Layer Metasurfaces," Jul. 17, 2018, Physical Review Applied , 10, pp. 014016-1 to 014016-12 (Year: 2018).

International Search Report and Written Opinion, mailed Nov. 5, 2019, issued in corresponding International Application No. PCT/US2019/046501, filed Aug. 14, 2019, 9 pages.

McDonald, B., "Surf2stl," MATLAB Central File Exchange, 2021, https://www.mathworks.com/matlabcentral/fileexchange/4512-surf2stl (Retrieved Feb. 14, 2021), 8 pages.

Melde, K., et al., "Holograms for Acoustics," Nature 537(7621):518-522, Sep. 2016.

Mellin, S.D., and Norin, G.P., "Limits of Scalar Diffraction Theory and an Iterative Angular Spectrum Algorithm for Finite Aperture Diffractive Optical Element Design," Optics Express 8(13):705-722, Jun. 2001.

Yosida, S. and Yamamoto, M., "Design and Evaluation of Diffractive Optical Elements: Optimization by Using Iterative Angular Spectrum Approach and Evaluation Based on Vector Diffraction Theory," in Baldini, F., et al. (eds.), Optical Sensors 2009. • Proceedings of SPIE (The International Society for Optical Engineering), 7356:73561Z-1-73561Z-8, May 2009.

Randad, A., "Design, Fabrication and Characterization of Ultrasound Transducers for Fragmenting Large Renal Calculi," master's thesis, University of Washington, Seattle, Washington, Nov. 2018, <University of Washington Research Works Archive, https://digital. lib.washington.edu/researchworks/handle/1773/43102>(retrieved on Sep. 26, 2019, 104 pages.

Harper, J.D., et al., "Focused Ultrasound to Expel Calculi from the Kidney: Safety and Efficacy of a Clinical Prototype Device," The Journal of Urology® 190:1090-1095, Sep. 2013.

Suomi. V., et al., "Full Modeling of High-Intensity Focused Ultrasound and Thermal Heating in the Kidney Using Realistic Patient Models," IEEE Transactions on Biomedical Engineering, 65(5):969-979, May 2018.

Chen, L., et al., "High Intensity Focused Ultrasound Ablation for Patients with Inoperable Liver Cancer," Hepato-Gastroenterology 62:140-143, 2015.

National Kidney Foundation Inc., "Kidney Stones" [internet], National Kidney Foundation Inc. [cited Mar. 18, 2018], 6 pages.

National Kidney Foundation Inc. , "Kidney Stone Treatment: Shock Wave Lithotripsy" [internet], National Kidney Foundation Inc. [cited Mar. 18, 2018 ], 6 pages.

Nikolic, V., and B. Kal Tenbacher, "Sensitivity Analysis for Shape Optimization of a Focusing Acoustic Lens in Lithotripsy," Applied Mathematics & Optimization 76(2): 261-301, 2017.

Oberlin, D.T., et al., "Contemporary Surgical Trends in the Management of Upper Tract Calculi," The Journal of Urology, 193(3):880-884, 2015.

Pishchalnikov, Y.A., et al., "Cavitation selectively reduces the negative-pressure phase of lithotripter shock pulses," Acoustics Research Letters Online 6(4):280-286, 2005.

Pishchalnikov, Y.A., and J.A. Mcateer, "Cavitation-induced streaming in shock wave lithotripsy," Proceedings of Meetings on Acoustics, vol. 19, 075032, pp. 1-9; The Journal of Acoustical Society of America 133(5):3315-3315, 2013.

Pishchalnikov, Y.A., et al., Why Stones Break Better at Slow Shockwave Rates Than at Fast Rates: In Vitro Study with a Research Electrohydraulic Lithotripter, Journal of Endourology 20(8):537-41, 2006.

Pishchalnikov, Y.A., et al. "Bubble proliferation in shock wave lithotripsy," The Journal of Acoustical Society of America 121(5):3081, 2007.

Pishchalnikov, Y.A., and J.A. Mcateer, "Gas content of the medium surrounding a stone has a significant effect on the efficiency of stone breakage in shock wave lithotripsy.," The Journal of Acoustical Society of America vol. 127, No. 3, 1761, 2010.

(56) References Cited

OTHER PUBLICATIONS

Randad, A., "Design, Fabrication and Characterization of Ultrasound Transducers for Fragmenting Large Renal Calculi," master's thesis, University of Washington, Seattle, Washington, Nov. 2018, < University of Washington Research Works Archive, https://digital.lib.washington.edu/researchworks/handle/1773/43102> Figure 3/1, pp. 32, 51, and 78.

Randad, A., et al., "Design, fabrication, and characterization of broad beam transducers for fragmenting large renal calculi with burst wave lithotripsy," The Journal of Acoustical Society of America 148(1):44-50, 2020.

Randad, A.P., et al., "Design of a Transducer for Fragmenting Large Kidney Stones Using Burst Wave Lithotripsy," Proceedings of Meetings on Acoustics 35(1):1-11, 2018.

Rassweiler, J.J., et al., "Shock Wave Technology and Application: An Update," European Urology 59(5):784-796, 2011.

Rosnitskiy, P.B., et al., "Design of HIFU Transducers for Generating Specified Nonlinear Ultrasound Fields," in IEEE Transactions on Ultrasonics, Ferroelectrics, and Frequency Control 64(2):374-390, 2017.

Sallam, A., et al., "Theoretical and experimental investigations on metallic acoustic lenses," Proc. SPIE vol. 11588, Active and Passive Smart Structures and Integrated Systems XV, 1158807, Mar. 2021.

Samoudi, M.A. et al., "Computational modeling of a single-element transcranial focused ultrasound transducer for subthalamic nucleus stimulation," Journal of Neural Engineering, vol. 16, No. 2, 026015, 2019, 13 pages.

Sapozhnikov, O.A., "A mechanistic analysis of stone fracture in lithotripsy.," The Journal of Acoustical Society of America 121(2):1190-202, 2007.

Scales, C.D., et al., "Prevalence of kidney stones in the United States," Urologic Diseases in America Project, European Urology 62(1):160-5, 2012.

Simon, J.C., et al., "Some Work on the Diagnosis and Management of Kidney Stones with Ultrasound," Acoustics Today 13(4):52-59, 2017.

Sonic Concepts, Inc., Therapy Transducers, <https://sonicconcepts.com/therapy-transducers/>, 2021.

Sorensen, M.D., et al., "Focused ultrasonic propulsion of kidney stones: review and update of preclinical technology.," Journal of Endourology 27(10):1183-1186, 2013.

Souquet, J., et al., "Design of Low-Loss Wide-Band Ultrasonic Transducers for Noninvasive Medical Application," IEEE Transactions on Sonics Ultrasonics 26(2):75-80, 1979.

Spirou, G.M., et al., "Optical and acoustic properties at 1064 nm of polyvinyl chloride-plastisol for use as a tissue phantom in biomedical optoacoustics," Physics in Medicine and Biology 50(14):N141-N153, 2005.

Srinivas, V., and R.L. Harne, "Acoustic wave focusing by doubly curved origami-inspired arrays," Mechanical Engineering, Journal of Intelligent Material Systems and Structures 31(8)1041-1052, 2020.

Starritt, H.C. et al., "An experimental investigation of streaming in pulsed diagnostic ultrasound beams," Ultrasound in Medical and biology 15(4):363-373, 1989.

Suomi, V. et al., "Full Modeling of High-Intensity Focused Ultrasound and Thermal Heating in the Kidney Using Realistic Patient Models," IEEE Transactions on Biomedical Engineering 65(5):969-979, 2018.

Thomas, G.P.L. et al., "Parametric Shape Optimization of Lens-Focused Piezoelectric Ultrasound Transducers," IEEE Transactions on Ultrasonics, Ferroelectrics, and Frequency Control 65(5):844-850, 2018.

Tiselius, H.G., et al., "Stone Burden in an Average Swedish Population of Stone Formers Requiring Active Stone Removal: How Can the Stone Size be Estimated in the Clinical Routine?" European Urology 43:275-281, 2003.

Ueno, A., et al., "Relation of Spontaneous Passage of Ureteral Calculi to Size," Urology 10(6):544-546, 1977.

Upsdell, S.M., et al., "Diuretic-induced urinary flow rates at varying clearances and their relevance to the performance and interpretation of diuresis renography.," British Journal of Urology 61(1):14-18, 1988.

Wang, M., et al., "Design and fabrication of diffractive microlens and analysis of optical characteristics," Proceedings of the SPIE, vol. 7657, id. 765717 (2010).

Worcester, E.M. et al., "Nephrolithiasis," Primary Care: Clinics in Office Practice 35(2):369-391, 2008.

Zhong, P., et al., "Recent Developments in SWL Physics Research," Journal of Endourology 13(9):611-617, 1999.

Zhou, Q., et al., "High efficiency acoustic Fresnel lens," Journal of Physics D: Applied Physics, vol. 53, No. 6, 065302, 2019, 7 pages.

Zwaschka, T.A., et al., "Combined Burst Wave Lithotripsy and Ultrasonic Propulsion for Improved Urinary Stone Fragmentation," Journal of Endourology 32(4):344-349, 2018.

Ali, C., et al., "Tunable Control and Functional Switch of Transmitted Acoustic Waves by an Arch-Shaped Metasurface," Chinese Journal of Theoretical and Applied Mechanics, 2021, 53(3): 789-801, 2021.

Al-Jumaily, A.M. et al., "On the Development of Focused Ultrasound Liquid Atomizers," Advances in Acoustics and Vibration, vol. 2017, pp. 1-10, 2017.

Bailey, M.R., et al., "Progress in Lithotripsy Research," Acoustics Today 2(2):18-29, 2006.

Armstrong, J. P. K. et al., "Engineering Anisotropic Muscle Tissue using Acoustic Cell Patterning," Adv. Mater. 2018, 30, 1802649, pp. 1-7.

Armstrong, J. P. K. and M. M. Stevens. "Using Remote Fields for Complex Tissue Engineering," Trends in Biotechnology, Mar. 2020, vol. 38, No. 3, pp. 254-263 <https://doi.org/10.1016/j.tibtech.2019.07.005>.

Baudoin M. et a., "Spatially selective manipulation of cells with single-beam acoustical tweezers," Nature Communications; 2020 11:4244, pp. 1-10 <https://doi.org/10.1038/s41467-020-18000-y>.

Chansoria, P. and R. Shirwaiker, "3D bioprinting of anisotropic engineered tissue constructs with ultrasonically induced cell patterning," Elsevier: Additive Manufacturing 32 (2020) 101042, pp. 1-12.

Chansoria, P. and R. Shirwaiker, "Characterizing the Process Physics of Ultrasound-Assisted Bioprinting," Scientific Reports 2019 9:13889, p. 1-17 <https://doi.org/10.1038/s41598-019-50449-w>.

Chansoria, P. et al., Ultrasound-assisted biofabrication and bioprinting of preferentially aligned three-dimensional cellular constructs, Biofabrication 11 (2019) 035015, pp. 1-18.

Cheng, K. W. et al., "Fast three-dimensional micropatterning of PC12 cells in rapidly crosslinked hydrogel scaffolds using ultrasonic standing waves," 2020 Biofabrication 12 015013.

Dardikman-Yoffe, G. et al. "High-resolution 4-D acquisition of freely swimming human sperm cells without staining," Sci. Adv. 2020; 6 : eaay7619 Apr. 10, 2020.

Ding, X. et al., "Tunable patterning of microparticles and cells using standing surface acoustic waves," Lab Chip, 2012, 12, 2491-2497.

Gesellchen, F. et al., "Cell patterning with a heptagon acoustic tweezer—application in neurite guidance," Lab Chip, 2014, 14, 2266.

Gu, Y. et al., "Acoustofluidic Holography for Micro- to Nanoscale Particle Manipulation," ACS Nano 2020, 14, 14635-14645.

Hampson, M., "Ultrasonic Holograms: Who Knew AcousticsCould Go 3D? Imaging and other medicalapplications waiting in the wings," News Sensors, Feb. 3, 2021.

Kim, H. N., "Patterning Methods for Polymers in Cell and Tissue Engineering," Annals of Biomedical Engineering, vol. 40, No. 6, Jun. 2012 (2012) pp. 1339-1355.

Imashiro, C.; Shimizu, T. "Fundamental Technologies and Recent Advances of Cell-Sheet-Based Tissue Engineering," Int. J. Mol. Sci. 2021, 22, 425. https://doi.org/ 10.3390/ijms22010425.

Joenathan, C. et al., "Lateral shear interferometer using multiplexed holographic lenses and spatial Fourier transform: varying spectrum position and phase fluctuations," Optical Engineering 52(8), 084103 (Aug. 2013).

(56) References Cited

OTHER PUBLICATIONS

Joenathan, C. et al., "Novel and simple lateral shear interferometer with holographic lens and spatial Fourier transform," Optical Engineering 51(7), 075601 (Jul. 2012).

Koo, K-i et al., "Acoustic Cell Patterning in Hydrogel for Three-Dimensional Cell Network Formation," Micromachines 2021, 12, 3. https://dx.doi.org/10.3390/ mi12010003.

Ma, Z. et al., "Acoustic Holographic Cell Patterning in a Biocompatible Hydrogel," Adv. Mater. 2020, 32, 1904181, pp. 1-6.

Murugan, Ph.D., R. and S. Ramakrishna, Ph.D., "Design Strategies of Tissue Engineering Scaffolds with Controlled Fiber Orientation," Tissue Engineering vol. 13: No. 8, 2007, Mary Ann Liebert, Inc., DOI: 10.1089/ten.2006.0078.

Physics World, "Holographic lenses focus ultrasound in the brain," Apr. 18, 2019.

Ren, X. et al., "Particle Trapping in Arbitrary Trajectories Using First-Order Bessel-Like Acoustic Beams," Physical Review Applied 15, 054041 (2021).

Shanjani, PhD, Y. et al., "Acoustic Patterning of Growth Factor for Three-Dimensional Tissue Engineering," Tissue Engineering: Part A, vol. 26, Nos. 11 and 12, 2020, Mary Ann Liebert, Inc., DOI: 10.1089/ten.tea.2019.0271.

Shi, J. et al., "Acoustic tweezers: patterning cells and microparticles using standing surface acoustic waves (SSAW)," Lab Chip, 2009, 9, 2890-2895.

Shipman, M. "Ultrasound Aligns Living Cells inBioprinted Tissues," Apr. 10, 2019; 4-min. read.

Yang, S. et al., "Harmonic acoustics for dynamic and selective particle manipulation," Nature Materials, vol. 21, May 2022, 540-546.

Stevens, M. M. et al., "Direct patterning of mammalian cells onto porous tissue engineering substrates using agarose stamps," Elsevier: Biomaterials 26 (2005) 7636-7641.

Tian, Z. et al., "Generating multifunctional acoustic tweezers in Petri dishes for contactless, precise manipulation of bioparticles," Tian et al., Sci. Adv. 2020; 6 : eabb0494 Sep. 9, 2020.

Wang, X. et al., "A method for solvent-free fabrication of porous polymer using solid-state foaming and ultrasound for tissue engineering applications," Elseier: Biomaterials 27 (2006) 1924-1929.

Comeau, Eric S. et al., "Ultrasound patterning technologies for studying vascular morphogenesis in 3D," Journal of Cell Science (2017) 130, 232-242; doi:10.1242/jcs.188151.

Dalecki, D. and D. C. Hocking, "Ultrasound Technologies for Biomaterials Fabrication and Imaging," Annals of Biomedical Engineering, vol. 43, No. 3, Mar. 2015 (2014) pp. 747-761; DOI: 10.1007/s10439-014-1158-6.

Falconnet, D. et al., "Surface engineering approaches to micropattern surfaces for cell-based assays," Elsevier: Biomaterials 27 (2006) 3044-3063.

Gjorevski, N. et al., "Designer matrices for intestinal stem cell and organoid culture," Nature vol. 539, Nov. 2016, 560-576; doi:10.1038/nature20168.

Hitchock, T. and L. Niklason, "Lymphatic Tissue Engineering Progress and Prospects," Ann N Y Acad Sci. 2008 ; 1131: 44-49. doi:10.1196/annals.1413.004.

Jaklenec, PH.D., A. et al., "Progress in the Tissue Engineering and Stem Cell Industry Are we there yet?" Tissue Engineering: Part B, vol. 18, No. 3, 2012, 155-167; DOI: 10.1089/ten.teb.2011.0553.

Jeon, H. et al., "Directing cell migration and organization via nanocrater-patterned cell repellent interfaces," Nat Mater. Sep. 2015 ; 14(9): 918-923. doi:10.1038/nmat4342.

Koo, K. et al., "Acoustic Cell Patterning in Hydrogel for Three-Dimensional Cell Network Formation," Micromachines 2021, 12, 3. https://dx.doi.org/10.3390/ mi12010003.

Olson, J. L. et al., "Tissue Engineering: Current Strategies and Future Directions," Chonnam Med J 2011;47:1-13; DOI: 10.4068/cmj.2011.47.1.1.

Rajagopalan, P. et al., "Direct Comparison of the Spread Area, Contractility, and Migration of balb/c 3T3 Fibroblasts Adhered to Fibronectin- and RGD-Modified Substrata," Biophysical Journal vol. 87 Oct. 2004 2818-2827.

Shanjani, PhD., Y. et al., "Acoustic Patterning of Growth Factor for Three-Dimensional Tissue Engineering," Tissue Engineering: Part A, vol. 26, Nos. 11 and 12, 2020, 602-612; DOI: 10.1089/ten.tea. 2019.0271.

Young, J. L. et al., Nanoscale and mechanical properties of the physiological cell—ECM microenvironment, Elsevier: Experimental Cell Research 343 (2016) 3-6.

Bakhtiari-Nejad, M., "Multi-focal transmission acoustic phase holograms in contactless ultrasonic power transfer systems," Sensors and Actuators A: Physical, vol. 340, 2022, 113551.

Bigelow, T.A., "Experimental Evaluation of Nonlinear Indices for Ultrasound Transducer Characterizations" master's thesis, Colorado State University, 1998, pp. 99-103, Appendix B: The KLM Model.

Blitz, B.F., et al., "Applicability of Iceland Spar as a Stone Model Standard for Lithotripsy Devices," Journal of Endourology 9(6):449-452, 1995.

Bohris, C., "Quality of Coupling in ESWL Significantly Affects the Disintegration Capacity—How to Achieve Good Coupling With Ultra-Sound Gel," in ed. C. Koehrmann et al., 1st ed., "Therapy Energy Applications in Urology II: Standards Recent Developments," Chap. 2.4, pp. 61-64, 2010.

Chan, W. et al., "Laser-generated focused ultrasound for arbitrary waveforms," Applied Physics Letters 109(17):174102, 2016.

Chaussy, C., et al., "Extracorporeally Induced Destruction of Kidney Stones by Shock Waves," The Lancet, vol. 316, No. 8207, pp. 1265-1268, 1980.

Chu, B.T.C., "Design of a defocused transducer for targeted cancer drug delivery by ultrasound-mediated hyperthermia, PhD thesis, University of Oxford," 2018, 215 pages.

Cleveland, R., et al., "The Physics of Shock Wave Lithotripsy," Smith's Textbook of Endourology, published by B. C. Decker Inc., Hamilton, Ontario, Canada, vol. 1, Chap. 38, pp. 317-331, 2007.

Crum, L.A., "Cavitation Microjets as a Contributory Mechanism for Renal Calculi Disintegration in ESWL," The Journal of Urology 140(6):1587-1590, 1988.

Crum, L.A., et al., "Acoustic cavitation generated by microsecond pulses of ultrasound," Nature, vol. 319, No. 6048, pp. 52-54, 1986.

Delius, M., et al., "A mechanism of gallstone destruction by extracorporeal shock waves.," Naturwissenschaften 75(4):200-201, 1988.

Duryea, A.P., et al., "In Vitro Comminution of Model Renal Calculi Using Histotripsy," IEEE Transactions on Ultrasonics Ferroelectrics and Frequency Control 58(5):971-980, 2011.

Eisenmenger, W., "The mechanisms of stone fragmentation in ESWL.," Ultrasound Medical Biology 27(5):683-693, 2001.

Eisenmenger, W. et al., "The first clinical results of 'wide-focus and low-pressure' ESWL," Ultrasound Medical Biology 28(6):769-774, 2002.

Esch, E., et al., "A simple method for fabricating artificial kidney stones of different physical properties," Urological Research 38(4):315-319, 2010.

Ferri, M., et al., "On the Evaluation of the Suitability of the Materials Used to 30 Print Holographic Acoustic Lenses to Correct Transcranial Focused Ultrasound Aberrations," Polymers 2019, 11(9), 1521, 25 pages.

Ferri, M., et al., "Enhanced Numerical Method for the Design of 3-D-Printed Holographic Acoustic Lenses for Aberration Correction of Single-Element Transcranial Focused Ultrasound," Ultrasound in Medicine and Biology 45(3):867-884, 2019.

Gao, H., et al., "Acoustic focusing by symmetrical self-bending beams with phase modulations," Applied Physics Letters, vol. 108, No. 7, 2016, 5 pages.

Hadimioglu, B., et al., "High-Efficiency Fresnel Acoustic Lenses," IEEE Ultrasonics Symposium, pp. 579-582, 1993.

He, J., et al., "Multitarget Transcranial Ultrasound Therapy in Small Animals Based on Phase-Only Acoustic Holographic Lens," in IEEE Transactions on Ultrasonics, Ferroelectrics, and Frequency Control 69(2):662-671, 2022.

(56) References Cited

OTHER PUBLICATIONS

Hsiao, Y.H., et al., "Clinical Application of High-Intensity Focused Ultrasound in Cancer Therapy," Journal of Cancer 7(3):225-231, 2016.

Hunter, C., et al., "Evaluation of in vitro burst wave lithotripsy exposure conditions," Scientific Program of 35th World Congress of Endourology Program Book and Abstracts, BRPS4: Bench to Bedside: The Science of Stones II—A37—Journal of Endourology, vol. 31, No. S2, paper BRPRS4-20, 2017.

Hwang, E.Y., et al., "Variables controlling contrast generation in a urinary bladder model," The Journal of the Acoustical Society of America 103(6):3706-3716, 1998.

Ikeda T., et al., "Cloud cavitation control for lithotripsy using high intensity focused ultrasound," Ultrasound in Medicine Biology 32(9):383-1397, 2006.

Jeong, J.S., et al., "Extended Necrosis by Using Dual-Curved Therapeutic Transducer for Noninvasive HIFU Surgery," 2011 IEEE International Ultrasonics Symposium, Orlando, Florida, 2011, pp. 2321-2324.

Jimenez-Gambin, S., et al., "Generating Bessel beams with broad depth-of-field by using phase-only acoustic holograms," Scientific Reports 9:20104, 2019, 13 pages.

Jimenez-Gambin, S., et al., "Holograms to Focus Arbitrary Ultrasonic Fields through the Skull," Physical Review Applied vol. 12, Issue 1, 2019, 14 pages.

Kim, G., et al., "Poroelastic microlattices for underwater wave focusing," Extreme Mechanics Letters vol. 49, 2021, 6 pages.

Kim, J., et al., "Acoustic holograms for directing arbitrary cavitation patterns," Applied Physics Letters vol. 118, No. 5, 2021, 7 pages.

Kim, J., et al., "Holographic acoustic admittance surface for acoustic beam steering," Applied Physics Letters, vol. 115, No. 19. 2019, 6 pages.

Kim, Y., et al., "Rapid Prototyping Fabrication of Focused Ultrasound Transducers," IEEE Transactions on Ultrasonics Ferroelectrics, and Frequency Control 61(9):1559-1574, 2014.

Krimholtz, R., et al., "New equivalent circuits for elementary piezoelectric transducers," Electronics Letters 6(13):398-399, 1970.

Lee, S., et al., "Preclinical study to improve microbubble-mediated drug delivery in cancer using an ultrasonic probe with an interchangeable acoustic lens," Scientific Reports 11:12654, 2021, 10 pages.

Levesque, D., et al., "Performance of Ultrasonic Imaging With Frequency Domain SAFT (F-SAFT)," Industrial Materials Institute, National Research Council Canada, Boucherville, Quebec, Canada, Sep. 2004, 8 pages.

Li, X.S., "Modulation of acoustic self-accelerating beams with tunable curved metasurfaces," Applied Physics Letters, vol. 118, No. 2, 2021, 6 pages.

Li, Z., et al., "Acoustic Hole-Hologram for Ultrasonic Focusing With High Sensitivity," in IEEE Sensors Journal 21(7):8935-8942, 2021.

Litwin, M.S., et al., "Urologic Diseases in America 2012," Washington, DC US Gov. Print. Office; NIH Publ. No. 12-7865, Tables: 11-2-11-42, 2012.

Liu, Y., et al., "BegoStone—a new stone phantom for shock wave lithotripsy research (L)," The Journal of Acoustical Society of America 112(4):1265-1268, 2002.

Marechal, P., et al., "Effect of Acoustical Properties of a Lens on the Pulse-Echo Response of a Single Element Transducer," 2004 IEEE International Ultrasonics Symposium Ferroelectrics, and Frequency Control Joint 50th Anniversary Conference, Montreal, Quebec, Canada, vol. 3, pp. 1651-1654.

Marzo, A., et al., "Holographic acoustic elements for manipulation of levitated objects," Nature Communications, vol. 6, No. 1, 9661, 2015, 7 pages.

Maslakowski, M.S., et al., "The Characterization and Assembly of an Efficient, Cost Effective Focused Ultrasound Transducer," 2020 IEEE 14th Dallas Circuits and Systems Conference (DCAS), Dallas, Texas, 2020, 6 pages.

Maxwell, A. D., et al., "Fragmentation of Urinary Calculi In Vitro by Burst Wave Lithotripsy.," The Journal of Urology 193(1): 338-44, 2015.

May, P.C., et al., "Detection and Evaluation of Renal Injury in Burst Wave Lithotripsy Using Ultrasound and Magnetic Resonance Imaging," Journal of Endourology 31(8):786-792, 2017.

Mayo Clinic, "Kidney stones diagnosis and treatment" [internet], [cited Mar. 18, 2018], 9 pages.

Mcdonald, B., "surf2stl—File Exchange—MATLAB Central." [Online]. Available: https:/lwww.mathworks.com/matlabcentral/fileexchange/4512-surf2stl, [Accessed: Jul. 22, 2018], 1 page.

Karzova, "Shock formation and nonlinear saturation effects in the ultrasound field of a diagnostic curvilinear probe", Acoustical Society of America, 2017 (Year: 2017).

* cited by examiner

METHOD TO CREATE PATTERNS IN TISSUE GROWTH FOR TISSUE ENGINEERING

CROSS-REFERENCE TO RELATED APPLICATION

This application claims the benefit of U.S. Provisional Application No. 63/395,029, filed Aug. 4, 2022, the disclosure of which is expressly incorporated herein by reference in its entirety.

STATEMENT OF GOVERNMENT LICENSE RIGHTS

This invention was made with government support under Grant No. P01 DK043881, awarded by the National Institutes of Health (NIH). The government has certain rights in the invention.

BACKGROUND

In tissue engineering, cells are aligned along defined structures that allow for cellular agglomeration and regeneration. Once the cells are aligned along specific planes at required thickness, tissue can be regenerated in vivo. For example, cells may be arranged in vitro for bioprinting the organs layer by layer.

Such alignment of the cells in tissue can be achieved by pressure and amplitude fields created by ultrasound. The conventional technology for aligning the cells relies on standing waves to make a pattern of pressures along which the cells are arranged, therefore enabling vessels to grow within the aligned cells, which is an important step in tissue engineering. Some conventional technologies rely on a travelling wave from a single transducer to push cells up against an existing tissue or other solid barrier by radiation force, thus agglomerating the cells along a surface. In some cases, the ultrasound waves reflect from the solid barrier, creating a pattern of standing waves that trap the cells. Other conventional technologies rely on two travelling waves transmitted from two transducers, where the two travelling waves combine to create a desired pattern of pressure fields. However, the conventional systems have limited capabilities in generating predetermined target arrangements of cells. Therefore, systems and methods for improved bonding of parts are still needed.

SUMMARY

This summary is provided to introduce a selection of concepts in a simplified form that are further described below in the Detailed Description. The summary is not intended to identify key features of the claimed subject matter, nor is it intended to be used as an aid in determining the scope of the claimed subject matter.

The inventive technology uses holographic beam shaping to produce a complex three-dimensional pressure field and a desired pattern of forces within a target volume. In response to the pressure and force patterns, the biological cells align in preferred directions, thereby promoting vessel growth within preferred formations and enabling a custom-designed vascular system for engineered tissue applications.

In operation, the ultrasound transducer may transmit the ultrasound through a holographic lens toward the target area. The transmitted ultrasound waves combine constructively and destructively to create pressure fields, for example a series of parallel planes of constant pressure that facilitate biological cells agglomeration, thus allowing for vascular tissue growth between the planes. These parallel planes of constant pressure can be aligned along the acoustic axis of the ultrasound transducer.

The holographic lens may be designed through an iterative angular spectrum approach (IASA) for designing lenses form the desired pattern imposed at a chosen distance from the acoustic source. The distance of the pattern from the source can be selected to maintain the pressure pattern over few wavelengths where the pressure term in the Gor'kov potential controls radiation forces resulting in minimal axial radiation forces on particles (e.g., biological cells) with similar density to surrounding medium. A combination of holographic lens and a single ultrasound transducer can produce desired cell patterns based on pressure and radiation force. In some embodiments, the ultrasound may be applied transcutaneously.

In operation, the biological cells (also referred to as cells for simplicity and brevity) are trapped in an elongated volume where one dimension is along the axis of the transducer and the other dimension is transverse to the axis. Particles that are much smaller than the ultrasound wavelength may be agglomerated along high-pressure regions based on the forces predicted using Gor'kov potential. Such cell agglomerations may allow for vascular tissue growth between the planes of constant pressure.

Therefore, with the present inventive technology a single source transducer coupled with a holographic lens may create an acoustic pattern for which the conventional technology would require multiple ultrasound transducers. Furthermore, use of a holographic lens allows an accurate control of phase distribution across the ultrasound source even at a subwavelength resolution (i.e., at a resolution that is smaller than a wavelength of ultrasound), which is normally not achievable with the conventional combinations of ultrasound transducers. Therefore, a combination of ultrasound and holographic lens is a relatively inexpensive and easily manufactured alternative for the arrays of ultrasound transducers.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Figure 1:
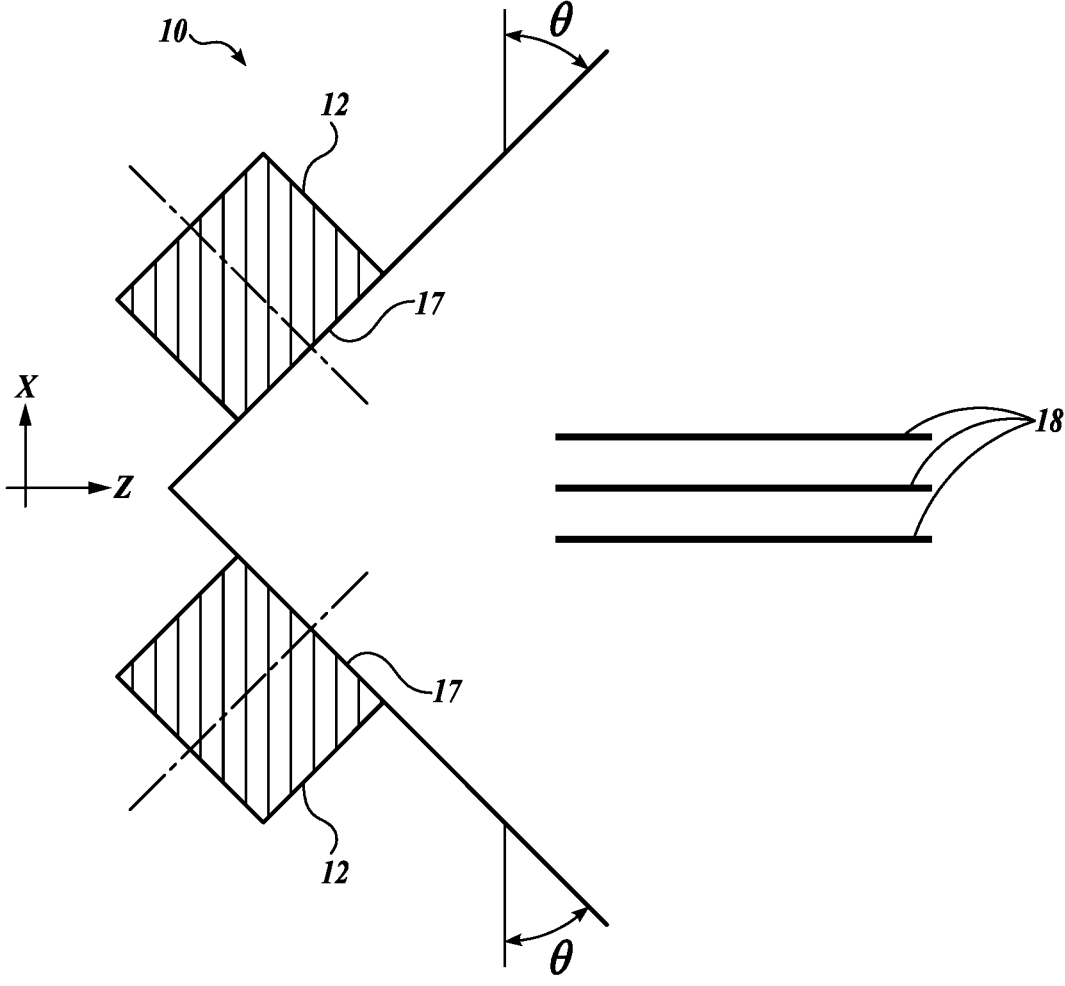
FIG. 1 is a schematic view of ultrasound standing waves generated in accordance with prior art technology.

FIG. 1 is a schematic view of ultrasound standing waves generated in accordance with prior art technology. The prior art system 10 relies on multiple ultrasound transducers 12. Axial centerlines of ultrasound transducers 12 are oriented normally against planes 17 that are mutually perpendicular, where each of the planes 17 is oriented at an angle θ with respect to a vertical direction X.

In operation, the ultrasound waves emitted by the ultrasound transducers 12 constructively and destructively combine to create standing waves 18, which are spaced at a distance $$\frac{\lambda}{2\sin\theta},$$

where λ is the wavelength or the ultrasound. The biological cells or other small objects can be aligned along the planes of the standing waves 18. However, conventional technology requires multiple transducers. Furthermore, the conventional technology is also limited by producing a relatively large spacing between the adjacent standing waves 18, such spacing having an order of magnitude that generally correspond to the wavelength λ of the ultrasound.

Figure 2:
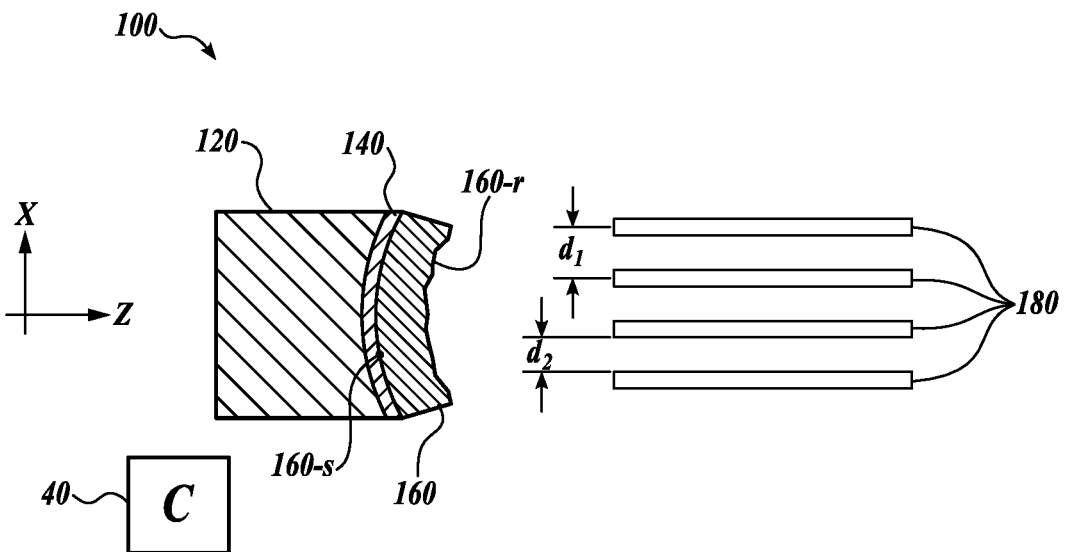
FIG. 2 is a schematic view of ultrasound field generated in accordance with embodiments of the present technology.

FIG. 2 is a schematic view of ultrasound field generated in accordance with embodiments of the present technology.

Illustrated system 100 includes a holographic lens 160 that is attached by an interface 140 to an ultrasound transducer 120.

In operation, the transducer 120 vibrates at ultrasound frequencies (e.g., from about 20 kHz to about 10 MHz, from about 1 MHz to about 4 MHz, etc.). The transducer 120 can include a piezoelectric element that expands and shrinks with changing electrical polarity applied to the transducer. Such a change in electrical polarity can be applied by an alternating current (AC) at a target ultrasound frequency. The operation of the transducer 12, including powering the transducer from the AC source, may be controlled by a controller 40.

In some embodiments, the customizable holographic lens is curved along its principal plane such that the holographic lens 160 conforms to the mating surface of the transducer 160, either directly or through an interface 140. For example, for the transducer 160 having a concave outside surface, the holographic lens may be correspondingly shaped such that the smooth surface 160-s of the holographic lens (i.e., the surface that is free of holographic features) mates with the outside surface of the transducer or with the interface material at the transducer. The holographic features on the opposite, non-mating side 160-r of the lens face the target area of the body.

In operation, the holographic lens 160 focuses the ultrasound generated by the transducer 120 onto a target area. The roughness on the non-mating side 160-r of the holographic lens 160 acts to create phase offsets that cause the ultrasound to constructively/destructively combine thus resulting constant pressure fields 180 along a predetermined pattern (e.g., along multiple parallel planes).

The illustrated constant pressure fields 180 (also referred to as parallel transverse planes) are vertical planes that are parallel to the ultrasound source (i.e., parallel to the axis of the transducer 120 along the Z direction). Therefore, the parallel transverse planes 180 extend axially in the Z direction, while also extending transversely along the Y-Z plane. The planes of constant pressure field 180 (i.e., parallel transverse planes 180) may be characterized by their mutual spacing d1 (e.g., 1.5 mm) and a kerf d2 between the planes (e.g., 0.5-0.8 mm). In some embodiments, the pressure field 180 may include multiple parallel laminates that are 10-44 mm high (extending orthogonally to the plane of paper of FIG. 2), the height corresponding to the transducer width. The parallel laminates of the pressure field may be characterized by positive peak pressure of 1 MPa, when ultrasound wavelength is within a range of 1.5 mm to 0.3 mm. In some embodiments, the spacing and kerf are selectable by adjusting the frequencies of the transmitted ultrasound. In different embodiments, design of the holographic lens may produce sub-wavelength (smaller than a wavelength of ultrasound) thickness of an individual constant pressure field 180. In the context of this application, the pressure field 180 is referred to as a constant pressure field 180, i.e., a pressure field having a zero axial gradient along individual high pressure zones of the constant pressure field. However, a person of ordinary skill would understand that some reasonable pressure gradient may still be present along the Z (axial) direction of the individual high pressure zones (parallel transverse planes) of the field 180 for as long as such pressure gradient corresponds to a small fraction (e.g., below 1%, 5% or 10%) of the pressure within the individual pressure field 180. Stated differently, the pressure fields 180 may be considered constant for as long as pressure variability or gradient of the pressure fields is below a predetermined threshold (e.g., below 1%, 5% or 10%). This predetermined threshold may be referred to as a first predetermined threshold.

By using a holographic lens 160 having a relatively uniform thickness (other than the thickness variations caused by the holographic features themselves) and a principal plane that follows the curvature of the mating surface of the transducer, the acoustic losses can be reduced and ultrasound targeting can be improved. Such improvements are at least in part based on reduction of the overall thickness of the holographic lens, which in turn reduces energy dissipation and improves targeting of the curved holographic lens (non-planar holographic lens). Improvements may also be based on the reduction of discontinuities on the surface with the holographic features, which in turn improves the accuracy of the desired results of phase and or pressure, resulting in a more precise outline of the constant pressure fields 180. In some embodiments, the customizable lens is produced by three-dimensional (3D) additive printing.

Figures 3A, 3B:
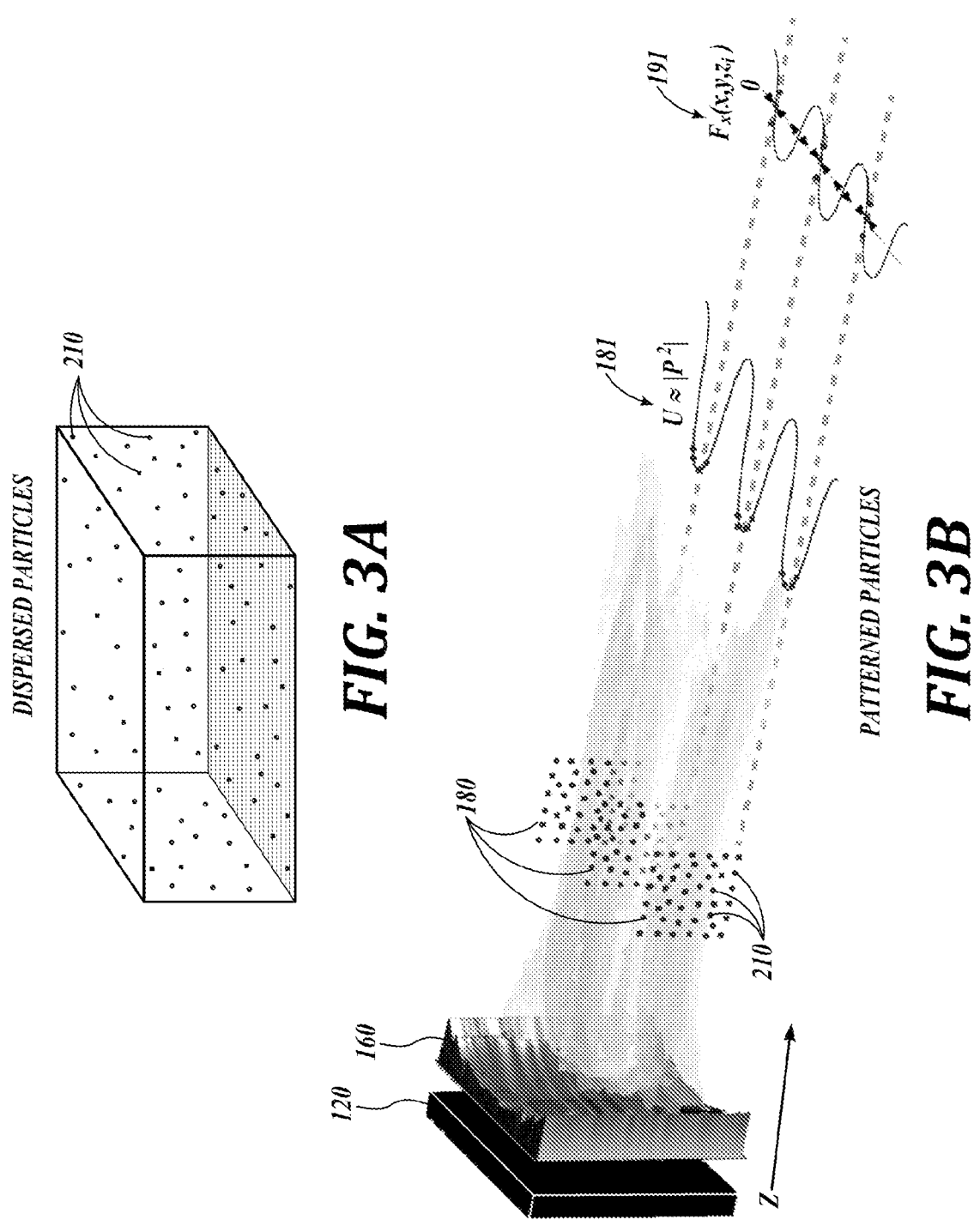
FIG. 3A is a schematic view of dispersed particles in accordance with embodiments of the present technology.
FIG. 3B is a schematic view of acoustic radiation forces aligning the particles along parallel planes of pressure in accordance with embodiments of the present technology.

FIG. 3A is a schematic view of dispersed particles in accordance with embodiments of the present technology. In absence of spatially varying pressures and/or forces exerted on the particles by, for example, ultrasound, particles 210 are distributed generally uniformly over a given volume. Some examples of such particles are tissue cells (biological cells), polystyrene microspheres, etc.

FIG. 3B is a schematic view of acoustic radiation forces aligning the particles along parallel planes of pressure in accordance with embodiments of the present technology. The transducer 120 and holographic lens 160 are shown in an exploded view. Generally, the holographic lens is attached to the transducer either directly or through interface material. The ultrasound waves that propagate through the holographic lens 160 combine in a constructive/destructive manner to generate planes 180 of constant (or generally constant) pressure along the axial (Z) direction the transducer, which is also a direction of propagation for ultrasound waves. The pressure planes 180 have no appreciable axial pressure gradient within the axial region of interest where the Gor'kov potential U is directly proportional to the pressure P for particles with density similar to the surrounding medium, as shown in a diagram 181 in FIG. 3B. Forces exerted on the particles are shown in a diagram 191. Therefore, the ultrasound waves operate in an open field, unlike with the conventional technology that uses a combination of transducers (as in FIG. 1) or a solid barrier (where a single transducer is aimed at the solid barrier) to create standing waves. The resulting forces along planes 180 tend to aggregate particles 210 along the planes 180.

A target location that is too close to, or too far from, the source and the phase hologram cannot synthesize and maintain uniform parallel pressure planes over a distance. Therefore, the imposed target pressure image location is generally placed in the translational region of the field, near the end of the Fresnel region and before the Fraunhofer diffraction region. This region allows the target image to be at a distance where the development of spherical spreading can maintain the shaped image for 2-3λ axial distance. For sources with the effective radius much larger than the wavelength, the translational region starts prior to the last on-axis pressure amplitude maximum. The phase boundary condition is unwrapped to achieve a continuously smooth morphology of the fabricated lens surface.

The field shaping may be confined to a nearfield region of the source before the spreading of the acoustic beam, which occurs proximal to the Rayleigh distance defined as the source area (i.e., area of the transmitting surface of the ultrasound transducer) over the wavelength of the ultrasound. The distance of manipulation is constrained by the source size and frequency, while the highest pressure pattern resolution is in some cases limited to λ/2. Sensitivity analysis of the source boundary conditions showed greater dependence on the phase than the amplitude boundary condition for higher pressure field accuracy. Phase unwrapping produces the most accurate phase boundary condition, but results in higher attenuation, causing weaker alignment forces of the outer planes. Therefore, the surface morphology chosen for the lens is important for accuracy.

The above mechanism of particle aggregation is explained with respect to the planar pressure fields 180. However, in different embodiments, based on the design of the holographic lens, the pressure fields 180 may be non-planar, i.e., curved.

Figure 4:
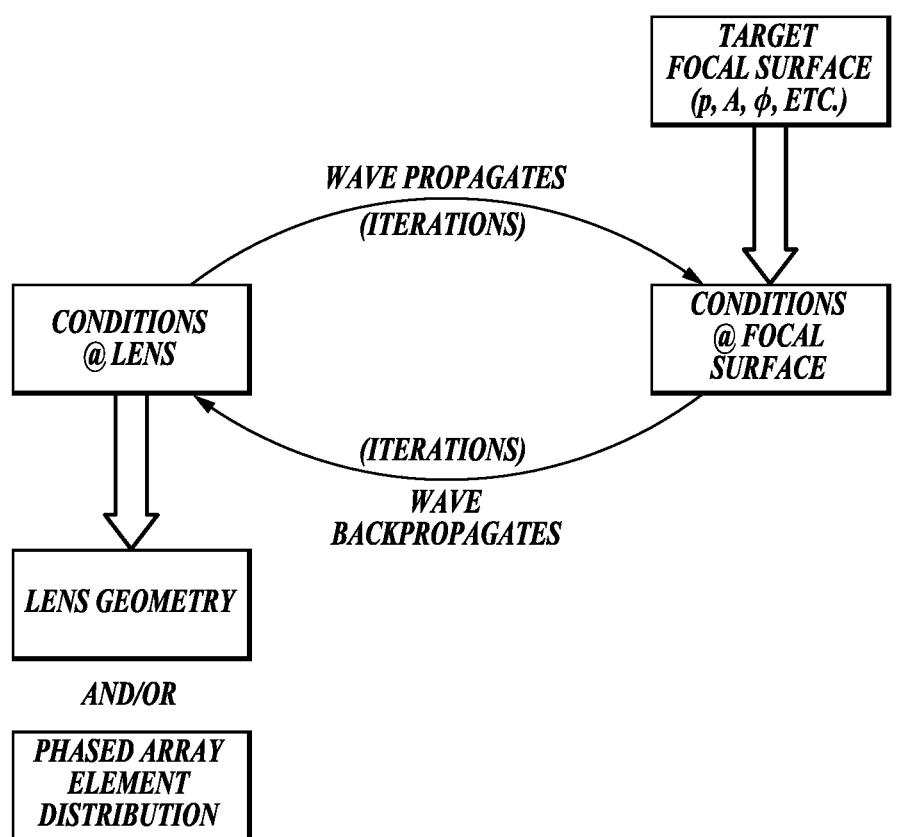
FIG. 4 is a schematic diagram of a method for designing a customizable lens in accordance with an embodiment of the present technology.

FIG. 4 is a schematic diagram of a method for designing a customizable lens in accordance with an embodiment of the present technology. In operations, the lens stimulates additive and destructive interference in a propagating wave front to generate a desired pressure and/or phase pattern at a target focal surface. The iterative angular spectrum approach (IASA) develops precise phase mappings for the lenses, which in turn provide a physical design for the lens geometry. As explained with reference to the conventional technology, typical approaches to lens design, such as the Fresnel approximation, fail to produce the desired pressure pattern with sufficient precision when the feature size in desired pressure pattern approaches the wavelength of the propagating wave front.

In some embodiments, the customizable lens may be designed using the iterative angular spectrum approach (IASA). In some embodiments, an algorithm implements IASA numerically by iteratively comparing simulated conditions at the target focal surface against the target conditions at the focal surface. In some embodiments, an algorithm implements IASA numerically by iteratively comparing simulated conditions at the focal surface against the target conditions at the focal surface; and the complex pressure distribution at the source to the results from the previous iterative step.

In a first step, the algorithm introduces lens geometry, propagating wave front, and target focal surface in a given medium. The target focal surface may be defined by its pressure pattern (p), made up of an amplitude map (A) and a phase map (Φ). The target focal surface is located some known distance from the lens.

The pressure wave equation includes amplitude and phase functions describing pressure at a given position in Euclidean space:

$$p(x, y, z) = \hat{p}(x, y, z)e^{j\Delta\Phi(x,y,z)} \quad (1)$$

where p(x, y, z) and ΔΦ(x, y, z) are the amplitude and phase functions, respectively.

The IASA method uses fast Fourier transform (FFT) and inverse fast Fourier transform (IFFT) methods to converge to an optimum error criterion, calculated as an error between the target focal surface and conditions at the focal surface. The general form of the FFT equation in Euclidean space is shown in Equation 2:

$$P(k_x, k_y) = \int\int_{-\infty}^{+\infty} p(x, y, 0)e^{-j(k_x x + k_y y)}dxdy \quad (2)$$

7

8

The output of the FFT equation, P(kx,ky), gives an angular spectrum, where ki is the wavenumber in i space. The IFFT equation, excluding the evanescent wave components, is shown in Equation 3:

$$p(x, y, z) = \frac{1}{4\pi^2} \int\int_{k_x^2+k_y^2\leq k^2} P(k_x,k_y)e^{j\left(k_xx+k_yy+\sqrt{k^2-k_x^2-k_y^2}\,z\right)}dk_xdk_y \qquad (3)$$

which provides the conditions at the focal surface in Euclidean space from the angular spectrum (P).

In the initial iteration of the loop shown in FIG. 4, the propagating wave front is transformed by FFT into an angular spectrum. A propagation function, shown in Equation 4, then calculates the effect of movement through a given medium on the angular spectrum:

$$P(k_x, k_y, z) = P(k_x, k_y, 0)e^{jz\sqrt{k^2-k_x^2-k_y^2}} \qquad (4)$$

which is used to calculate both propagation and back-propagation through the given medium between the focal surface and the lens. The propagating wave front then propagates through the lens and the given medium to produce an angular spectrum for a propagated wave front at the focal surface (the conditions at the focal surface).

As shown in FIG. 4, IFFT provides a wave equation in spatial coordinates for comparison to the desired conditions at the target focal surface. The error criterion indicates whether the lens design at the current iteration produces the target focal surface. In initial iterations, the error between the conditions at the focal surface and the target focal surface may be significant, due to near field effects that impact the propagating wave front.

To account for the near field effects, the IASA incorporates a back-propagation of the propagated wave front from the focal surface to the lens, shown as a clockwise lower arrow in FIG. 4, and modulates the propagating wave front, and its angular spectrum, for iterative propagation forward to the focal surface. The algorithm retains the latest iteration of the phase information at the focal surface to calculate convergence.

In addition to conventional IASA method, the method uses the multiple checks in the convergence criterion to meet our desired goals. The algorithm iteratively compares the convergence of the simulated conditions to the target image specified at each target location. Second, after the first iteration step and in parallel to the previous check, the algorithm compares the complex pressure distribution at the source to that of the previous step as well to speed up and improve the convergence calculation criterion. The comparisons in the previous two checks are specified to be within a specific error tolerance below which convergence to the optimal hologram solution is achieved. Finally, a maximum number of iterations is determined for each run, such that when it is exceeded the method terminates and saves the optimal hologram solution. The error tolerance and maximum number of iterations is determined based on the complexity of the hologram, such as, the number of target locations for phase and or amplitude at different frequencies. These checks of convergence are checked at each iteration step to yield the optimal solution.

Incorporating back propagation into an iterated forward propagating wave equation permits a more precise calculation of the conditions at the focal surface for subsequent adjustment of the lens geometry. With each cycle of forward propagation and back propagation the conditions at the focal surface and the conditions at the lens converge to an optimal solution.

An output of the IASA algorithm is the lens geometry. As described in Equation 5, a spatial thickness parameter describes the lens geometry by taking into account the transmission coefficient ($\alpha$) of the system, including acoustic impedances (Z) of the lens material (h), the given medium (m), and a transducer (t), a source of acoustic waves:

$$\alpha_T(x, y)) = \frac{4Z_tZ_h^2Z_m}{z_h^2(Z_t + Z_m)^2\cos(k_hT(x, y))^2 + \left(Z_h^2 + Z_tZ_m\right)^2\sin(k_hT(x, y))^2} \qquad (5)$$

The thickness of the lens (T) can be calculated from the angular spectrum of the converged solution by creating a phase map for the surface of the lens. The lens creates constructive and destructive interference in the near-field by introducing phase offsets ($\Delta\Phi$) in the propagating wave front as it passes through the holographic lens. The thickness of the lens is described as follows in Equations 6-7:

$$\Delta\Phi(x, y) = (k_m - k_h)\Delta T(x, y)) \qquad (6)$$

$$\text{where } T(x, y) = T_0 - \Delta T(x, y). \qquad (7)$$

The IASA algorithm is capable of designing a lens that produces multiple target focal surfaces at as many distances from the lens in a given medium. To accomplish this, the IASA algorithm separately incorporates the backpropagation from the wave equations of each of the target focal surfaces when modulating the propagating wave equation.

The IASA method can be used with different transducer geometries. For instance, for a focused transducer, the exact pressure field can be simulated and verified through holographic scanning in a plane. Next, the pressure field at the transducer aperture (obtained by back-projection) is used as the initial boundary condition over which we can impose the required phase to obtain the desired beam shape.

When compared to the conventional lens design methods, the IASA-based design method maximizes the power of the beam while producing an arbitrary pressure distribution in the plane of interest. Furthermore, the method can be extended to constrain the amplitude distribution in several different planes of propagation. Analogously, the method can be extended to produce different beam patterns using ultrasonic transducers at different frequencies. The method can also be used to constrain the phase distribution in one or more planes, or both amplitude and phase distributions simultaneously.

Figure 5A:
FIG. 5A is a cross-section of thickness of a holographic lens in accordance with embodiments of the present technology.

FIG. 5A is a cross-section of thickness of a holographic lens in accordance with embodiments of the present technology. The illustrated cross-section is shown prior to a possible curving of the holographic lens 160 against the curvature of the ultrasound transducer. Holographic features 165 on the non-mating side 160-r of the holographic lens can be designed based on, for example, the IASA method described with reference to FIG. 4 above.

Figure 5B:
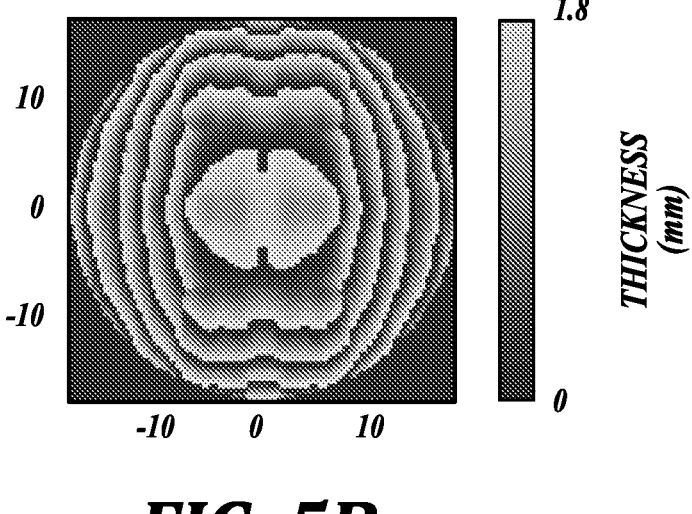
FIG. 5B is a diagram of phases on an outer surface of a holographic lens in accordance with embodiments of the present technology.

FIG. 5B is a diagram of phases on an outer surface of a holographic lens in accordance with embodiments of the present technology. The presence of the holographic features 165 causes localized differences in the phase of ultrasound waves that propagate from the mating side 160-*s* toward the non-mating side 160-*r* of the holographic lens. In operation, holographic features 165 cause localized phase delays for the ultrasound waves, resulting in differing phases at the side 160-*r* of the holographic lens, which in turn causes destructive/constructive combination of the ultrasound wave amplitudes.

Figure 5C:
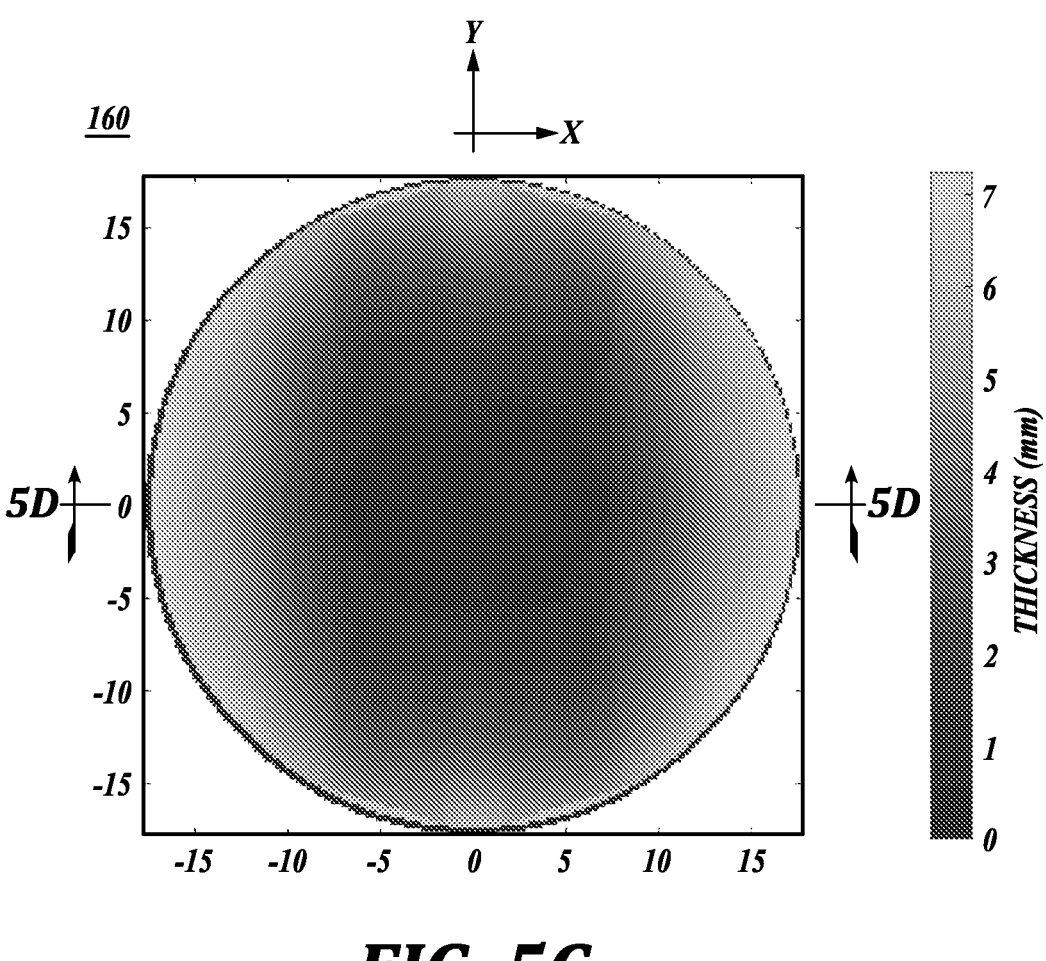
FIG. 5C is a thickness plot of a holographic lens in accordance with embodiments of the present technology.

FIG. 5C is a thickness plot of a holographic lens in accordance with embodiments of the present technology. FIG. 5C corresponds to an unwrapped lens, and FIG. 5B corresponds to a wrapped lens.

Figure 5D:
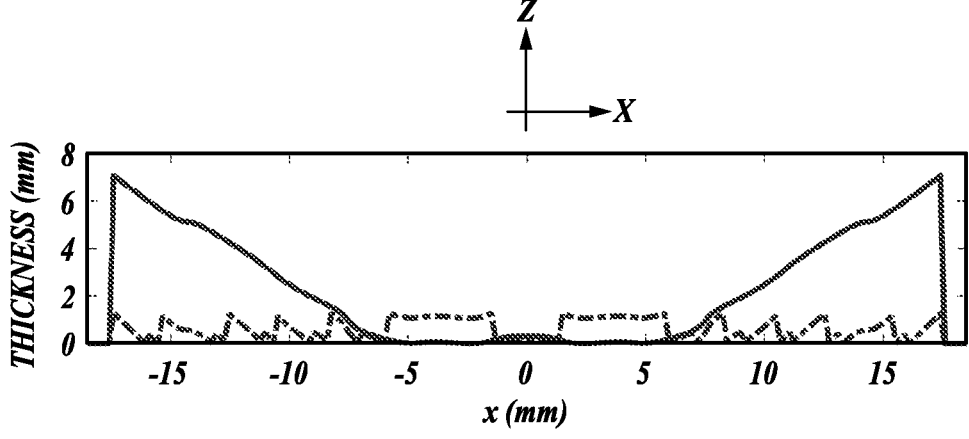
FIG. 5D is a cross-section of thickness of a holographic lens in accordance with embodiments of the present technology.

FIG. 5D is a cross-section D-D of a holographic lens. In particular, the solid line corresponds to the unwrapped lens of FIG. 5C and the dash line corresponds to the wrapped lens of FIG. 5B.

In some embodiments, the thickness of the holographic plates runs generally constant in Y direction, which is a direction into the plane of paper for the cross-sectional view of FIG. 5D, and an up and down direction for the top view of the holographic lens shown in FIG. 5C. Therefore, the illustrated holographic lens is thinner in the vicinity of Y axis that runs through the center of the holographic lens, and generally thicker when moving in the +X and −X directions away from the Y axis. When mated with the ultrasound transducer, this centerline Y of the holographic lens determines the orientation of the constant pressure fields 180, as shown, for example, in FIG. 7 below. That is, for the holographic lens illustrated in FIGS. 5C and 5D, the constant pressure fields 180 are oriented parallel to planes Y-Z.

In some embodiments, a lens unwrapping method may be used for the holographic lens design to eliminate thickness inaccuracies (also referred to as stepping inaccuracies), thus leading to a more accurate final pressure field. Although lens unwrapping can lead to lower pressure intensities in the peripheral regions of the target focal region, this approach maintains the majority of the field in the central regions. Additionally, advancements in 3D lens fabrication techniques allows for better material properties that are less attenuative and can eliminate this loss of energy.

Figure 6B:
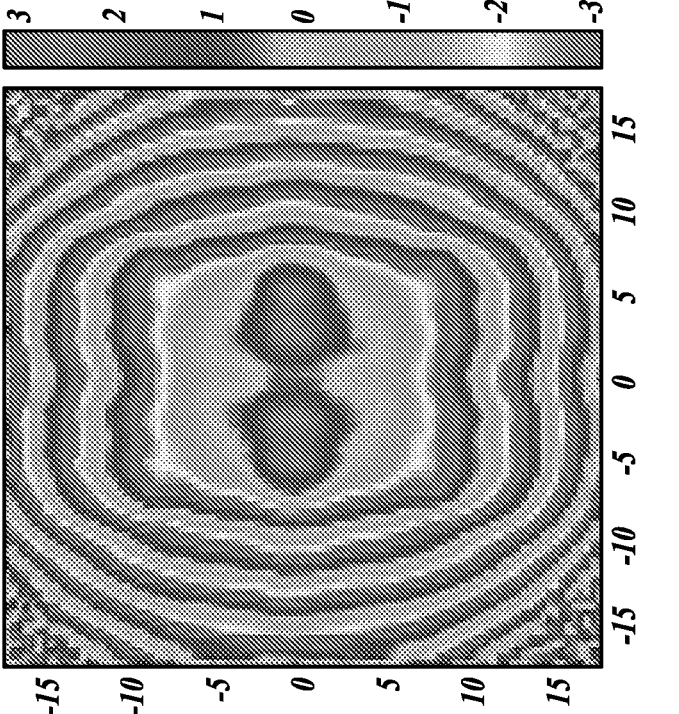
FIG. 6B is a graph of measured source phase for a holographic lens in accordance with embodiments of the present technology.
Figure 6A:
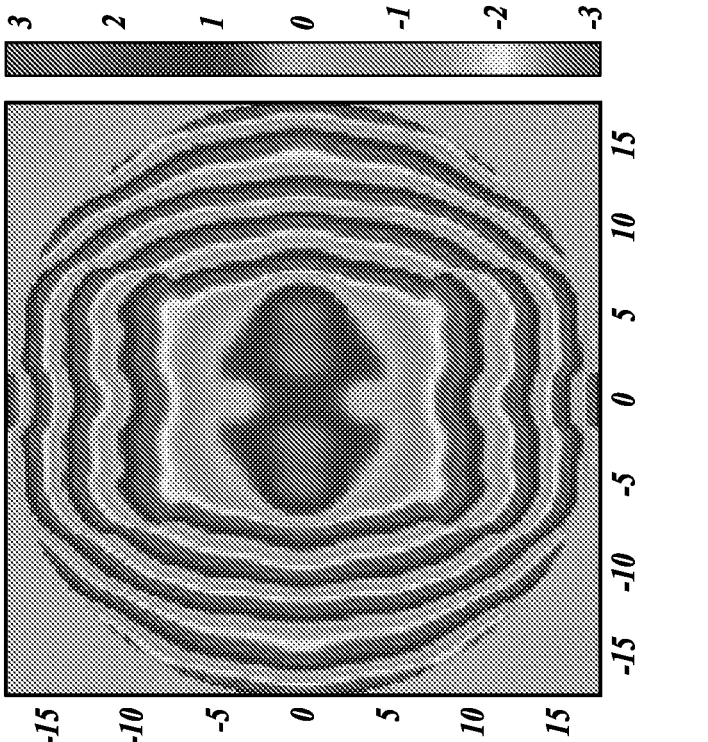
FIG. 6A is a graph of simulated source phase for a holographic lens in accordance with embodiments of the present technology.

FIGS. 6A and 6B are respectively graphs of simulated and measured source phase for a holographic lens in accordance with embodiments of the present technology. In some embodiments, the simulated source phase (FIG. 6A) is used to fabricate the lens producing the pressure distribution required for cell patterning.

Figure 7:
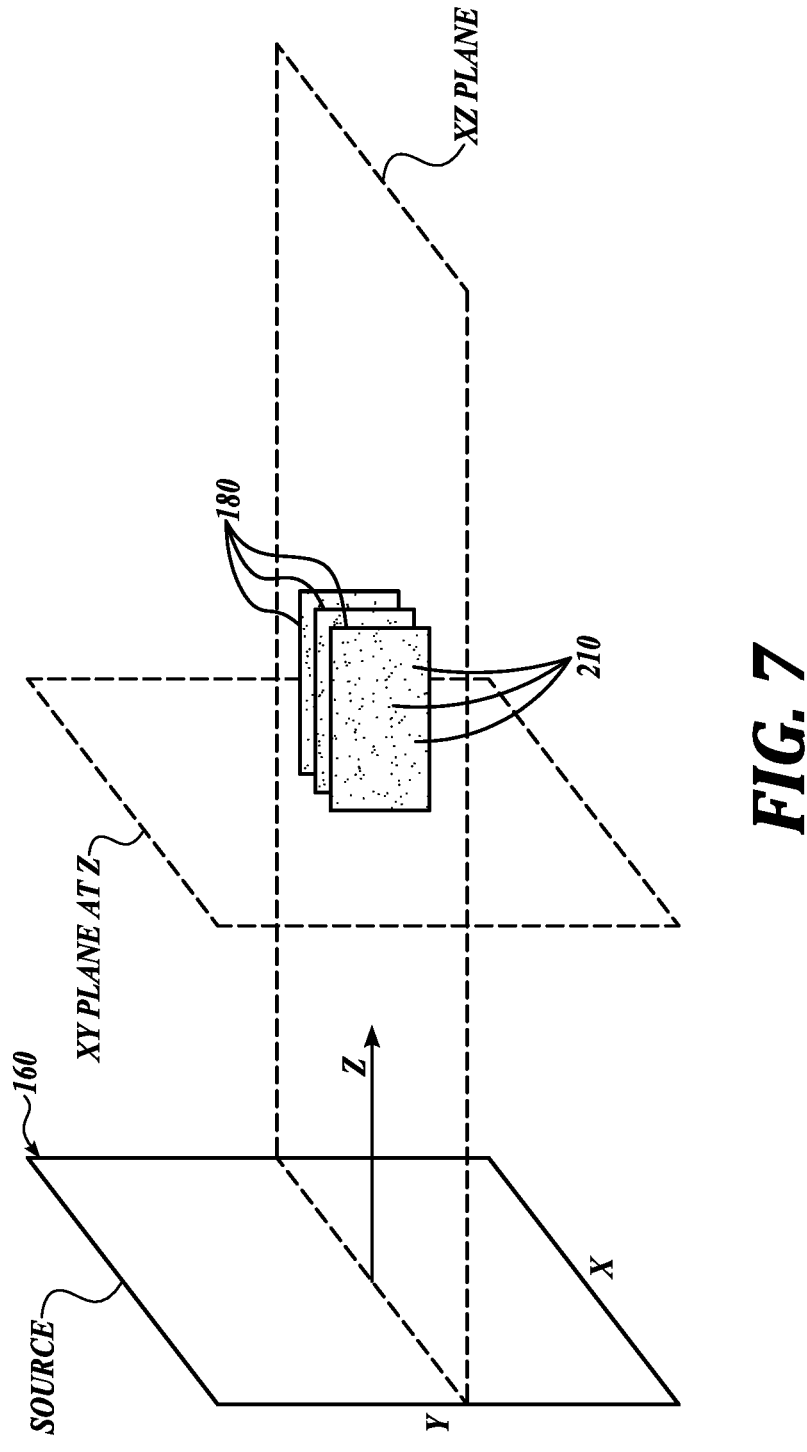
FIG. 7 is a schematic view of parallel planes of acoustic pressure in accordance with embodiments of the present technology.

FIG. 7 is a schematic view of parallel planes of constant acoustic pressure in accordance with embodiments of the present technology. In the illustrated embodiment, the source lies in the xy-plane. The axial plane is parallel to the acoustic axis and it bisects the source or may be understood as the xz-plane where y=0. The xy-transverse plane is a plane parallel to the source of ultrasound. Several experimental and simulation results are explained below with respect to the setup shown in FIG. 6.

Figure 8B:
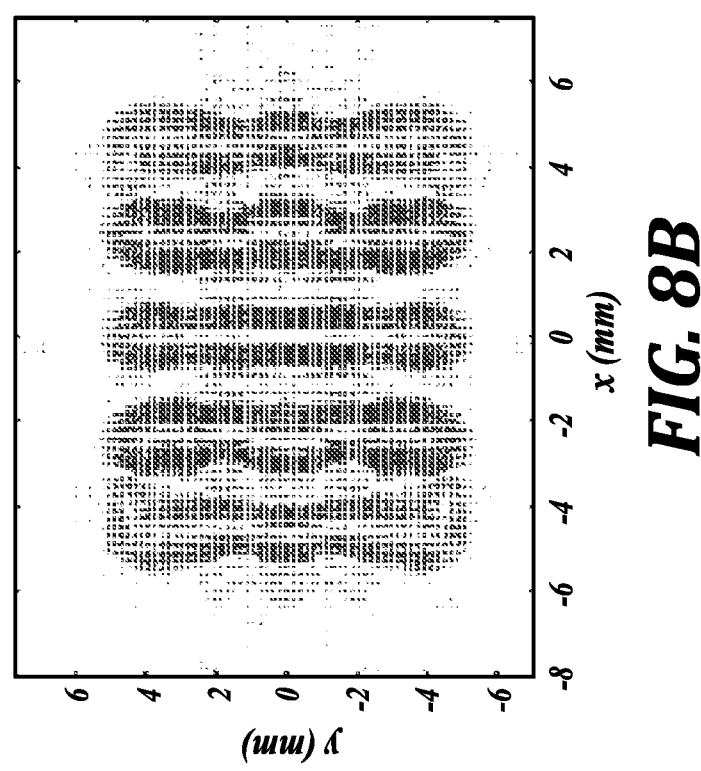
FIG. 8B is a graph of simulated radiation force in X-direction generated by a holographic lens in accordance with embodiments of the present technology.
Figure 8A:
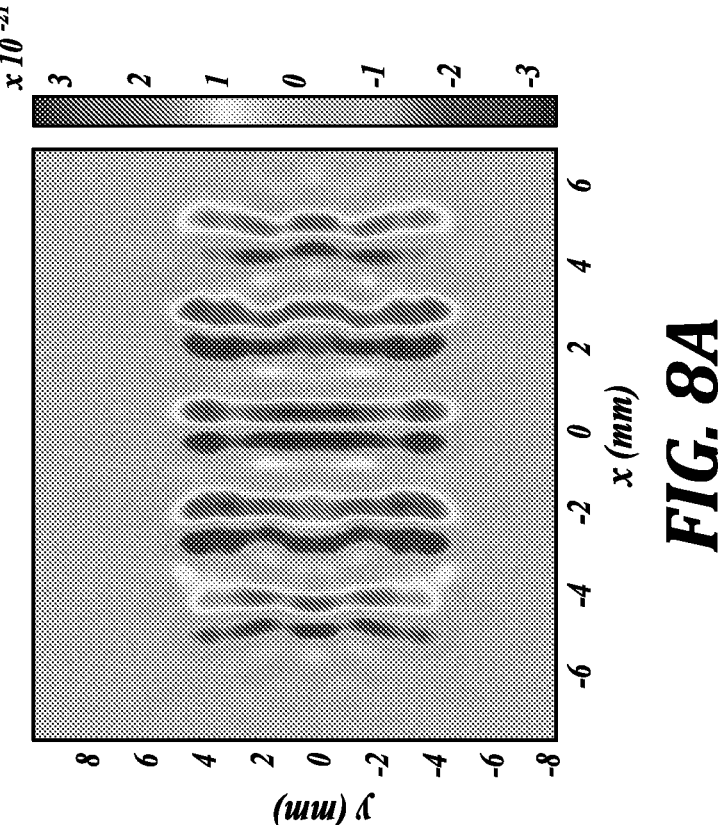
FIG. 8A is a graph of simulated two-dimensional distribution of the radiation force in the x direction generated by a holographic lens in accordance with embodiments of the present technology.

FIG. 8A is a graph of simulated radiation forces generated by a holographic lens in accordance with embodiments of the present technology. FIG. 8B is a graph of simulated radiation force in X-direction generated by a holographic lens in accordance with embodiments of the present technology. The radiation forces generate stable trapping regions that hold the biological cells (also referred to as cells for simplicity and brevity). Distribution of the radiation forces in the X-Y plane defines the shape of zero pressure gradient pressure field. Therefore, lateral pressure gradients in the Y direction within the parallel transverse planes X-Z may be larger than a predetermined threshold (also referred to as a second predetermined threshold). In operation, the cells are trapped by the lateral pressure gradients, i.e., between the adjacent, but opposite, lateral radiation forces as shown in FIG. 8B.

Figure 9A:
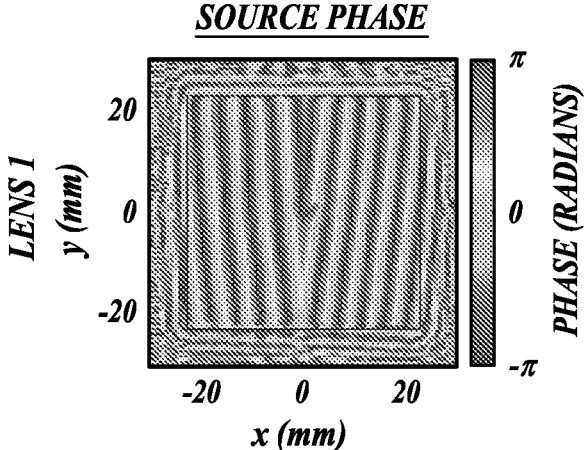
FIGS. 9A-9C show experimentally obtained distribution of source phases generated by holographic lenses in accordance with embodiments of the present technology.
Figure 9B:
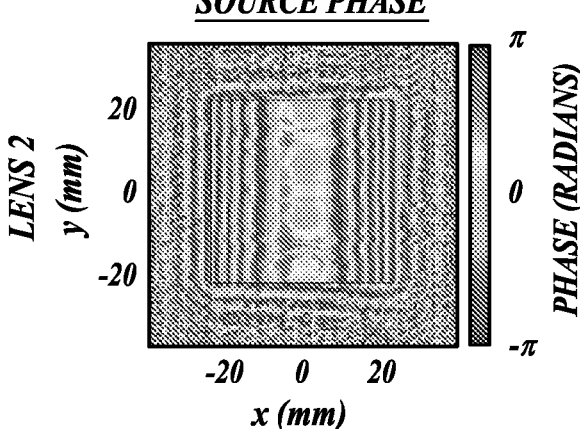
Figure 9C:
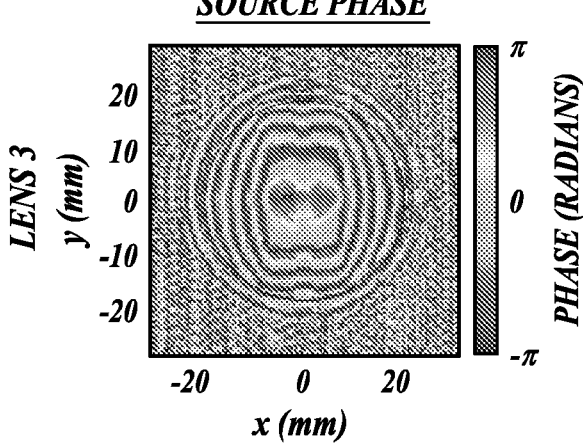
Figure 10A:
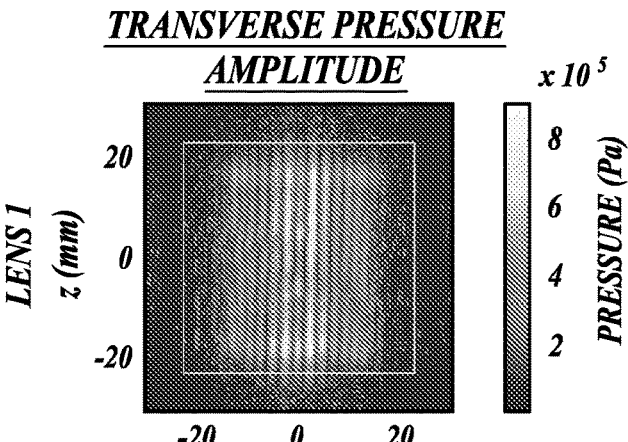
FIGS. 10A-10C show experimentally obtained distribution of transverse pressure amplitude generated by holographic lenses in accordance with embodiments of the present technology.
Figure 10B:
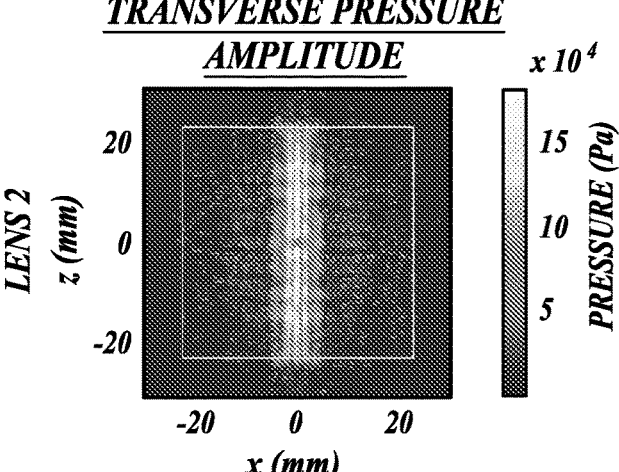
Figure 10C:
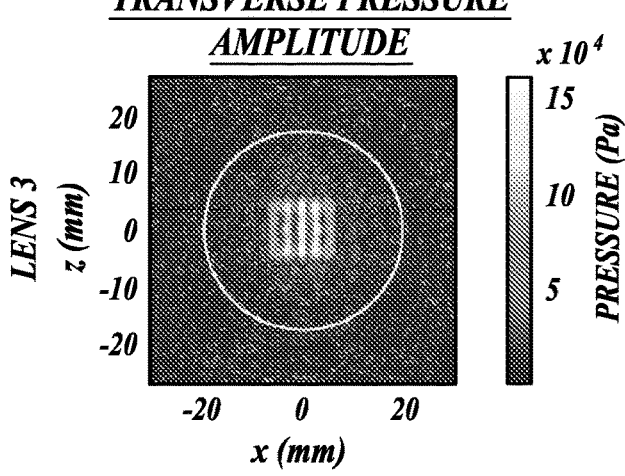
Figure 11A:
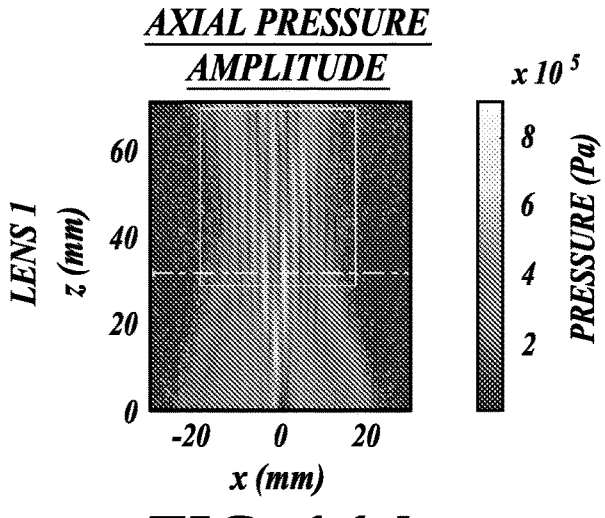
FIGS. 11A-11C show experimentally obtained axial pressures generated by holographic lenses in accordance with embodiments of the present technology.
Figure 11B:
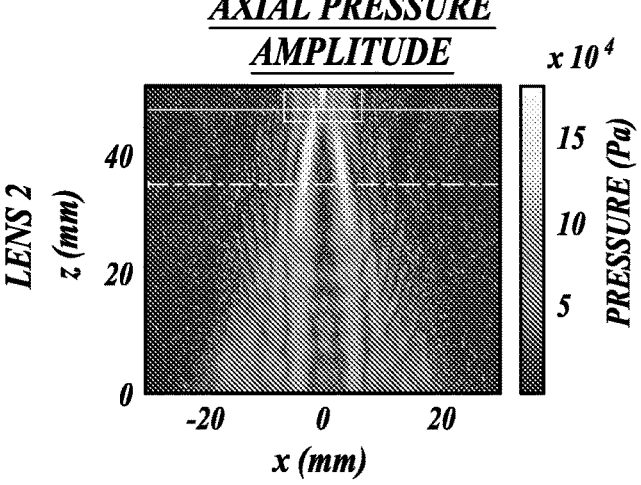
Figure 11C:
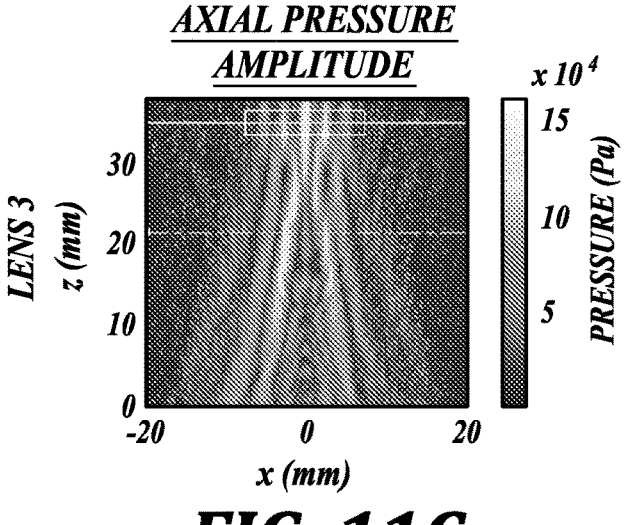

FIGS. 9A-9C show experimentally obtained distribution of source phases, FIGS. 10A-10C show experimentally obtained distribution of transverse pressure amplitude, and FIGS. 11A-11C show experimentally obtained axial pressure amplitude.

FIGS. 9A, 10A and 11A correspond to an experimental setup that uses a shape of a negative prism that bisects the lens at the middle. Therefore, FIGS. 9A, 10A and 11A are based on a combination of one transducer and a negative prism lens (also referred to as a lens 1 in the context of FIGS. 9A, 10A and 11A). In particular, the lens used in conjunction with FIGS. 9A, 10A and 11A has the shape of a negative prism with an angle of $2(90°-\theta_1)$. The lens was designed such that the apex of the negative prism bisects the lens at the middle. Thus, creating two plane sources intersecting at 60 degrees creates the desired interference acoustic planes. The lens was bonded to a 4.5×4.5 cm 1.5-MHz piezoelectric element. Such design produces a standing wave component along the transverse dimension and forward propagating wave along the acoustic axis creating parallel pressure planes that are spaced by $d_0=\lambda/(2*\sin(\theta_1-\theta_2))$, where $\theta_2$ is the angle of refraction at which the acoustic rays enter water, rather than $\theta_1$, due to the acoustic impedance mismatch between the lens material and the medium (water), and is calculated from Snell's law, $\sin \theta_1/c_1=\sin \theta_2/c_2$, where $c_1$ and $c_2$ are the speed of sound in the lens and medium. Therefore, based on this correction, the true angle separating the acoustic axes is $2(\theta_1-\theta_2)$ rather than $2\theta_1$ where the spacing would be $d=\lambda/(2*\sin \theta_1)$ if no lens was present and two sources were directly angled to directly output into water instead. The distance $d_0$ was used to calculate $\theta_2$ for comparison with theoretical predictions. The lens was 3D-printed from Rigid Transparent VeroClear material (Stratasys, Valencia, CA) with $\rho=1.2$ g/cm$^3$ and c=2560 m/s.

FIGS. 9B, 10B and 11B correspond to an experimental setup that uses holographic lens (also referred to as a lens 2) coupled to a 4.5-cm square source. FIGS. 9C, 10C and 11C correspond to an experimental setup that uses holographic lens (also referred to as a lens 3) coupled to a 3.5-cm circular source. The holographic lenses were designed using IASA method described in conjunction with FIG. 4. For both holographic lenses, a desired image is imposed at a plane parallel to the source and located at a specific distance away. For lens 2, the image plane was imposed along the acoustic axis 46 mm away from the source plane, and for lens 3 the image plane was imposed along the acoustic 35 mm away m the source plane. The iterative solution was initialized with a uniform pressure amplitude boundary condition at the source while allowing the phase distribution to vary until convergence in the source phase was reached, therefore achieving the desired imposed pressure image. The convergence criterion was reached when the change in the two-dimensional norm of the phase distribution at the source between the last two iterations is <0.001. The phase distribution boundary condition was unwrapped to get a continuous phase profile and eliminate the discontinuities due to phase wrapping using a global planar method based on the transport intensity equation. Lens 2 was 3D printed from Acura 60 (3D Systems Inc., Rock Hill, SC) with $\rho=1.21$ g/cm$^3$ and c=2570 m/s and lens 3 from Somos PerForm (Covestro, Pittsburgh, PA) with $\rho=1.65$ g/cm$^3$ and c=3278.4 m/s.

In all cases shown in FIGS. 9A-11C, approximately 0.3 grams of polyethylene microspheres were placed in a glass bottle with few drops of liquid detergent added as a surfactant, then 125 mL of deionized and degassed water was added to the bottle. A magnetic bar was inserted into the bottle, and it was continuously stirred by a magnetic mixer throughout the experiments. The microspheres were placed few drops at a time in a cuvette 3D-printed from polylactic acid (PLA) filament (Ultimaker, Farmingham, MA) with acoustically transparent side walls from 12.7 μm polyester clear film (McMaster-CARR). The cuvette was held in tank filled with degassed water. A green laser diode module was used to generate a 1.2 mm thick sheet perpendicular to the acoustic axis of the transducer to illuminate the suspended microspheres for visualization. All transducers were operated in a pulsed mode, transmitting 100-cycle pulses at 10% duty cycle. The microspheres alignment along the nodal planes created scattering of the light and were visible. A camera was placed outside the tank facing the transducer to capture the alignment.

The results show the field pressure measurements from the holography scan to compare the pressure outputs of the lenses, the calculation of the acoustic radiation forces on polyethylene microspheres, and the microspheres alignment in the pressure field. The three-dimensional pressure field was reconstructed from backward propagation to the source phase, and forward propagation from the scan plane.

For lens 1 (FIGS. 9A, 10A and 11A), the formation of standing wave pattern along the lens's transverse horizontal dimension extends with robust axial planes formation from 20 to 45 mm. The distance $d_0$ between the planes was measured to be 2.67±0.030 mm, while theory predicted 2.22 mm for an error of 2.15% and the angle of entry into the water from the lens was calculated from $d_0$ to be 12.75±0.17°, while theory predicted 13.0°. This deviation from prediction is attributed to the source phase produced by lens 1, as it can be seen that the phase has an independent tilt in each half of the lens at some oblique angle. The tilt imperfection was caused by wet sanding of the lens's surface in the preparation process. It was not possible to apply the tilt phase correction as such correction is applicable only to single planar tilt of the whole lens surface. At the given input voltage, maximum measured amplitude was 0.9 MPa.

The source phase correction for holographic lens 2 (FIGS. 9B, 10B and 11B) and holographic lens 3 (FIGS. 9C, 10C and 11C) removed the planar tilt from the non-orthogonality between the hydrophone axis and the lenses' vibrating surfaces. The experimentally measured source phase from both lenses 2 and 3 matches closely the source phase simulation. However, lens 2 phase shows irregularities that were possibly introduced from nonuniformities in the matching layer packed below the lens. The measured desired pressure image was formed at 48 and 35.6 mm for lens 2 and 3, rather than 46 and 35 mm being an expected design value. This is due to the mismatch between the sound speed in water and the lens material, which the simulation does not account for. The maximum measured amplitudes were 0.15, and 0.14 MPa for lenses 2 and 3 for their respective voltage input. In the obtained pressure image, the formation of 3 distinct planes from lens 2 was achieved, while the outer planes were weekly formed. The three center planes extended for 2.5 mm and had similar pressure level over the center 1.5 mm axial extent. For the 0.5 mm pre and post the 1.5 mm region, the planes had varying pressure levels with the center plane having increasing intensity to the adjacent planes as we move farther from the source. Similarly, lens 3 as predicted formed 5 parallel axial planes extending over a 1.5 mm with the outer planes forming at lower intensity level than was predicted by simulation. Feature Similarity Index (FSI) analysis was used to quantify the agreement between simulation and experimental pressure results, where an FSI of unity is achieved when the results are an exact match, and zero for lack thereof. The FSI score for lens 1, 2 and 3 was 0.950, 0.939, and 0.95, respectively.

Although the phase deviations from simulation for the holographic lenses was minimal, deviation from the desired pressure field was present. We investigated deviations of the pressure results from simulation, and the sensitivity of the results to the source phase and amplitude by testing virtual sources using different boundary conditions. Two virtual sources using: 1) measured phase and simulation amplitude, and 2) simulation phase and measured amplitude, were propagated to the image plane for comparison. A visual inspection of the results, from the virtual source using simulation phase and measured amplitude, showed full illumination was achieved, but with randomly distributed high-pressure regions in the field. Results from measured phase and theoretical amplitude exhibited the overall desired outline of the simulation with attenuated pressure output toward the edges of the pressure image. FSI score was used to determine the performance of the two virtual sources. For lens 2, the FSI improved from 0.939 to 0.941 and 0.961 for simulation amplitude and measured phase, and simulation phase and measured amplitude virtual sources, while for lens 3, it improved from 0.953 to 0.960 and 0.982. The results confirmed and pointed to the higher sensitivity to the phase than amplitude boundary condition. Additionally, experimental source amplitude was found to be nonuniform contradictory to what was imposed by IASA, and with higher attenuated output from the thicker regions of the holographic lenses.

Figure 12:
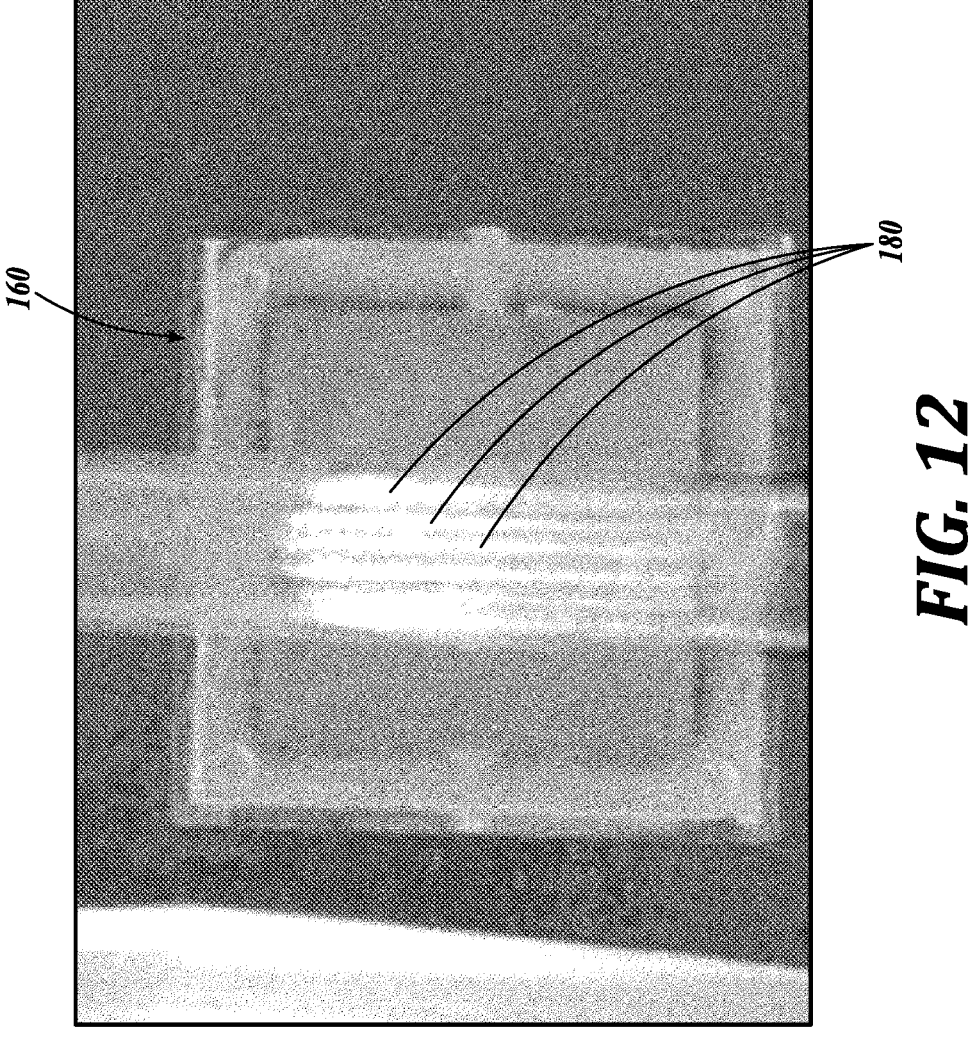
FIG. 12 shows experimentally obtained distribution of particles with an embodiment of the present technology.

FIG. 12 shows experimentally obtained distribution of particles with an embodiment of the present technology. Here, a column of water includes particles dispersed therein, where the distribution of the particles is shown by their green fluorescence. Behind the column is an ultrasound transducer with a holographic lens designed to create vertical axial planes of high pressure to agglomerate the particles. Before the ultrasound transducer starts to transmit, the particles are distributed evenly through the test cell. About 44 seconds later after the ultrasound being applied to the column causes the particles to agglomerate in the designed pattern, as shown in FIG. 12.

The terms used in the embodiments of the present disclosure are merely for the purpose of describing specific embodiment, rather than limiting the present disclosure. The terms "a", "an", "the", and "said" in a singular form in the embodiments of the present disclosure and the attached claims are also intended to include plural forms thereof, unless noted otherwise.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Such computers, controllers and data processors may include a non-transitory computer-readable medium with executable instructions. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Where methods are described, the methods may include more, fewer, or other steps. Additionally, steps may be performed in any suitable order. Accordingly, the disclosure can encompass other embodiments not expressly shown or described herein. In the context of this disclosure, the term "about," approximately" and similar means +/−5% of the stated value.

For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

What is claimed is:

1. A method for arranging biological cells along a predetermined pattern using an ultrasound, the method comprising:

emitting the ultrasound by an ultrasound transducer;

transmitting the ultrasound through a holographic lens toward a plurality of biological cells;

generating a pressure field in the predetermined patterns, wherein the predetermined pattern comprises a plurality of mutually parallel transverse planes, wherein the parallel transverse planes are configured to entrap groups of biological cells of the plurality of biological cells, wherein axial pressure gradients within the parallel transverse planes are smaller than a first predetermined threshold, and wherein lateral pressure gradients within the parallel transverse planes are larger than a second predetermined threshold; and in response to generating the pressure field, aligning the groups of entrapped biological cells within parallel transverse planes.

2. The method of claim 1, wherein the ultrasound transducer operates in an open field.

3. The method of claim 1, wherein the mutually parallel transverse planes are arranged along an axial direction.

4. The method of claim 3, wherein the axial pressure gradients within the parallel transverse planes are about zero.

5. The method of claim 3, wherein thicknesses of individual parallel transverse planes are smaller than a wavelength of the ultrasound.

6. The method of claim 3, wherein the parallel transverse planes have a height of 10-44 mm.

7. The method of claim 6, wherein the the height of the parallel transverse planes corresponds to a width of the transducer.

8. The method of claim 3, wherein the pressure fields the parallel transverse planes are configured in a nearfield region of the ultrasound transducer, wherein the nearfield corresponds to a Rayleigh distance defined as a ratio of a source cross sectional area over a wavelength of the ultrasound.

9. The method of claim 1, wherein the holographic lens comprises lens features at subwavelength sizes.

10. The method of claim 1, wherein the holographic lens is attached to the transducer via an interface.

11. The method of claim 10, wherein the interface comprises epoxy.

12. The method of claim 1, wherein the transducer is configured to transmit the ultrasound within a frequency range from 1 MHz to 4 MHz.

13. The method of claim 1, wherein the transducer is configured to transmit the ultrasound within a wavelength range from 1.5 mm to 0.3 mm.

14. A system for arranging biological cells along predetermined patterns using an ultrasound, the system comprising:

an ultrasound transducer; and a holographic lens attached to the ultrasound transducer, wherein the ultrasound transducer is configured for:

transmitting the ultrasound through the holographic lens toward a plurality of biological cells;

generating a pressure field in the predetermined patterns, wherein the predetermined pattern comprises a plurality of mutually parallel transverse planes, wherein the parallel transverse planes are configured to entrap groups of biological cells of the plurality of biological cells, wherein axial pressure gradients within the parallel transverse planes are smaller than a first predetermined threshold, and wherein lateral pressure gradients within the parallel transverse planes are larger than a second predetermined threshold; and in response to generating the pressure field, aligning the groups of entrapped biological cells within parallel transverse planes.

15. The system of claim 14, wherein the mutually parallel transverse planes are arranged along an axial direction.

16. The system of claim 15, wherein the axial pressure gradients within the parallel transverse planes are about zero.

17. The system of claim 16, wherein the holographic lens comprises lens features at subwavelength sizes, and wherein thicknesses of individual parallel transverse planes are smaller than a wavelength of the ultrasound.

18. The system of claim 14, wherein a transverse height of the parallel transverse planes corresponds to a width of the transducer.

19. The system of claim 14, wherein the holographic lens is attached to the transducer via an interface that comprises an epoxy.

20. The system of claim 14, wherein the transducer is configured to transmit the ultrasound within a frequency range from 1 MHz to 4 MHz.

21. The system of claim 14, wherein the transducer is configured to transmit the ultrasound within a wavelength range from 1.5 mm to 0.3 mm.

* * * * *